US010071990B2

(12) United States Patent
Tuttle et al.

(10) Patent No.: US 10,071,990 B2
(45) Date of Patent: Sep. 11, 2018

(54) SITE-SPECIFIC ORTHOGONAL LABELING OF THE CARBOXY TERMINUS OF α-TUBULIN IN LIVE CELLS

(71) Applicant: The Research Foundation for The State University of New York, Binghamton, NY (US)

(72) Inventors: Susan Bane Tuttle, Vestal, NY (US); Kamalika Mukherjee, Binghamton, NY (US)

(73) Assignee: The Research Foundation for The State University of New York, Binghamton, NY (US)

( * ) Notice: Subject to any disclaimer, the term of this patent is extended or adjusted under 35 U.S.C. 154(b) by 1063 days.

(21) Appl. No.: 14/293,417

(22) Filed: Jun. 2, 2014

(65) Prior Publication Data
US 2014/0356894 A1    Dec. 4, 2014

Related U.S. Application Data

(60) Provisional application No. 61/830,319, filed on Jun. 3, 2013.

(51) Int. Cl.
*G01N 33/50*    (2006.01)
*C07D 405/14*    (2006.01)

(52) U.S. Cl.
CPC .................. *C07D 405/14* (2013.01)

(58) Field of Classification Search
None
See application file for complete search history.

(56) References Cited

U.S. PATENT DOCUMENTS 5,798,276 A    8/1998    Haugland et al.
5,846,737 A    12/1998    Kang
(Continued)

FOREIGN PATENT DOCUMENTS

WO    WO2010033011 A1    3/2010

OTHER PUBLICATIONS

J. Thom, D. Anderson, J. McGregor and G. Cotton, Recombinant Protein Hydrazides: Application to Site-Specific Protein PEGylation, 2011, Bioconjugate Chem., vol. 22, pp. 1017-1020.*
(Continued)

*Primary Examiner* — Deirdre Renee Claytor
*Assistant Examiner* — Trent R Clarke
(74) *Attorney, Agent, or Firm* — Tully Rinckey PLLC; Steven M. Hoffberg

(57) ABSTRACT

A technique is provided to visualize microtubules in live cells that does not require genetic manipulation or microinjection. Moreover, this method also avoids perturbation of the endogenous microtubule network that occurs with taxol treatment. This technique exploits tyrosination and detyrosination of tubulin, a posttranslational modification cycle specific to the C-terminus of α-tubulin. Specifically, cells are grown in medium supplemented with a tyrosine derivative possessing a reactive functional group. The cellular enzyme tubulin tyrosine ligase attaches the unnatural amino acid to a single site on tubulin. Addition of fresh medium containing a suitably derivatized fluorophore then yields fluorescent tubulin, which incorporate into cellular microtubules. Importantly, the tubulin labeling approach demonstrated here does not detrimentally affect microtubule network or cell morphology. Thus we present a simple, robust labeling technique that allows microscopic analysis of microtubules in live cells.

20 Claims, 13 Drawing Sheets

(56) References Cited

U.S. PATENT DOCUMENTS

| | | | |
|---|---|---|---|
| 5,847,162 A | 12/1998 | Lee et al. | |
| 5,981,564 A | 11/1999 | Page et al. | |
| 6,017,712 A | 1/2000 | Lee et al. | |
| 6,025,505 A | 2/2000 | Lee et al. | |
| 6,080,852 A | 6/2000 | Lee et al. | |
| 6,562,632 B1 | 5/2003 | Szalecki et al. | |
| 6,716,979 B2 | 4/2004 | Diwu et al. | |
| 7,435,755 B2 | 10/2008 | Konopleva et al. | |
| 7,795,305 B2 | 9/2010 | Konopleva et al. | |
| 2003/0119732 A1 | 6/2003 | Konopleva et al. | |
| 2006/0016369 A1* | 1/2006 | Wu | C09D 11/34 106/31.29 |
| 2009/0093447 A1 | 4/2009 | Konopleva et al. | |
| 2010/0147913 A1 | 6/2010 | Corets | |
| 2012/0041017 A1 | 2/2012 | Lafanechere et al. | |
| 2014/0141452 A1 | 5/2014 | Watt et al. | |

OTHER PUBLICATIONS

Sebastian van de Linde, Steve Wolter, and Markus Sauer, Single-molecule Photoswitching and Localization, 2011, Aust. J. Chem., vol. 64, pp. 503-511.*

Abhijit Banerjee, Timothy D. Panosian, Kamalika Mukherjee, Rudravajhala Ravindra, Susannah Gal, Dan L. Sackett, and Susan Bane, "Site-Specific Orthogonal Labeling of the Carboxy Terminus of α-Tubulin", ACS Chem Biol. Aug. 20, 2010; 5(8): 777-785. doi:10.1021/cb100060v (see See abstract, pp. 778-784 and figures 1-7.).

International Search Report PCT/US2014/040520 (dated Apr. 29, 2015).

Wu, Liangxing, Design, Syntheses and Applications of Fluorescent Dyes, D. Phil. Dissertation Texas A&M Aug. 2009.

* cited by examiner

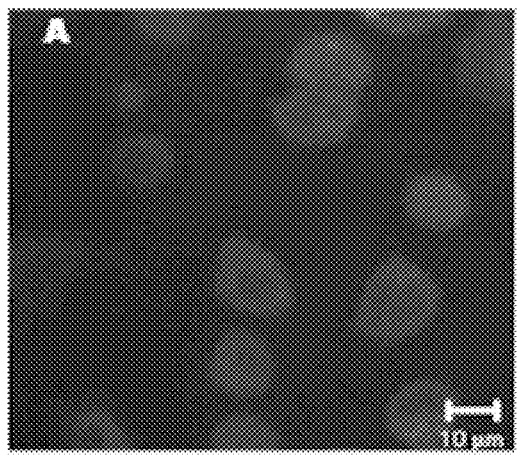
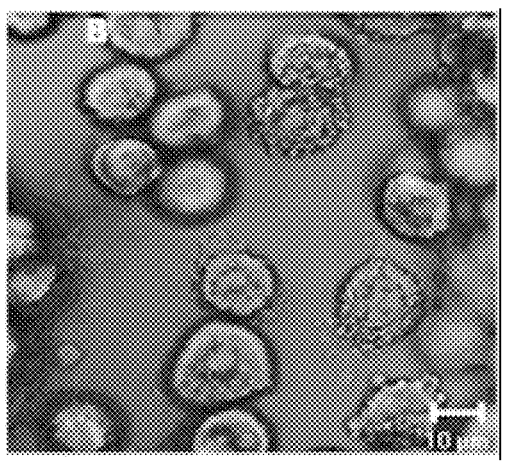
Fig. 6A                    Fig. 6B
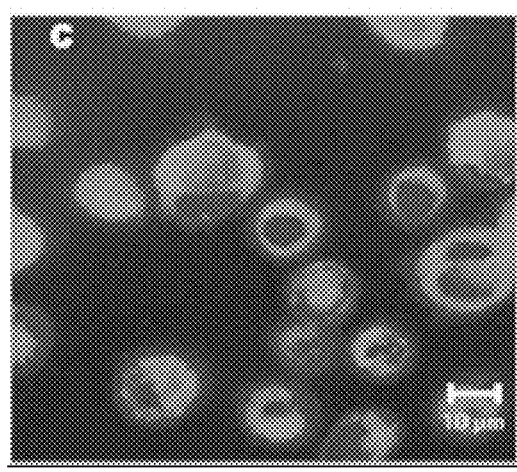
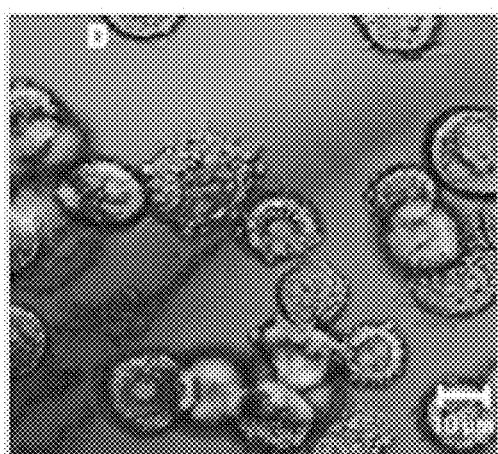
Fig. 6C                    Fig. 6D

SITE-SPECIFIC ORTHOGONAL LABELING OF THE CARBOXY TERMINUS OF α-TUBULIN IN LIVE CELLS

CROSS REFERENCE TO RELATED APPLICATION

The present application claims benefit of priority under 35 U.S.C. § 119(e) from U.S. Provisional Patent Application No. 61/830,319, filed Jun. 3, 2013, the entirety of which is expressly incorporated herein by reference in its entirety.

STATEMENT OF GOVERNMENT SUPPORT

This invention was made with government support under contract GM093941 awarded by the National Institutes of Health. The Government has certain rights in the invention.

BACKGROUND

Microtubules are a fundamental component of the cytoskeleton of eukaryotic cells and are associated with virtually any activity of a cell that involves movement (1). They are part of the mitotic spindle in mammalian cells, and their proper organization is essential for normal cell processes. Although microtubules perform heterogeneous tasks in cells, their basic structure is uniform. The core of the microtubule is entirely composed of tubulin, a 100 kDa heterodimer that assembles to form dynamic cylindrical structures (2).

The carboxy-terminal 15-20 amino acids of each tubulin subunit are the primary locus of sequence heterogeneity in an otherwise highly conserved protein. Tubulin is subject to extensive posttranslational modifications, including acetylation, polyglutamylation, polyglycylation, phosphorylation, tyrosination, and palmitoylation (for recent reviews, see refs 3 and 4). With the exception of acetylation, all of these posttranslational modifications take place in the carboxyterminal peptides of each subunit. Little is known about the structure of these peptides; they are not observable in the electron or X-ray diffraction structures of tubulin (5, 6). These peptides contain an abundance of glutamic acid residues and so are highly negatively charged at physiological pH. Molecular modeling supports the earlier hypothesis that the carboxy termini extend into solution perpendicularly to the microtubule central axis (7), but there are no experimental data that directly address this question.

A posttranslational event that is unique to tubulin is removal and replacement of the C-terminal tyrosine of α-tubulin (8). In this process, the genetically encoded tyrosine is cleaved by an unknown carboxypeptidase and replaced by the enzyme tubulin tyrosine ligase (TTL). TTL has been isolated from brain tissue, and the human version has been cloned and expressed, but the carboxypeptidase(s) involved in the detyrosination reaction has not yet been identified (9, 10). In vivo, microtubules containing detyrosinated tubulin (Glutubulin) are more stable than those containing tyrosinated tubulin (Tyr-tubulin) (11). Detyrosination does not affect the dynamic or drug-binding properties of purified tubulin (12), and detyrosination of tubulin does not stabilize microtubules in vitro (13); thus, the presence or absence of the α-tubulin carboxy-terminal tyrosine affects the association of nontubulin proteins with cellular microtubules rather than their intrinsic dynamicity. Although the purpose of the enzymatic cycle is not well understood, it is essential for the life of the cell. There is clear evidence that the tyrosination/detyrosination cycle is critical for neuronal organization and may influence tumorigenesis and tumor invasion. For example, TTL null mice undergo normal embryonic development but die shortly after birth (11). Poor patient prognosis has been correlated with elevated levels of Glu-tubulin in breast and prostate tumors and in neuroblastomas (14-16).

Tubulin, the major component of microtubules, undergoes a posttranslational modification that is unique to this protein. The carboxy terminal amino acid on just one of the highly homologous subunits of the tubulin heterodimer is hydrolyzed and replaced by a cycle of two specific enzymes. Tubulin tyrosine carboxypeptidase (TTCP) removes the genetically encoded C-terminal tyrosine from polymerized tubulin, exposing a glutamic acid residue. Tubulin tyrosine ligase (TTL) catalyzes peptide bond formation between this glutamic acid and tyrosine, and this enzyme acts preferentially on tubulin in its depolymerized state. TTL has been isolated and cloned, but nothing is known about the sequence and structure of TTCP. This post-translational modification cycle is critical for neuronal network organization and its disruption can also affect tumorigenesis. TTL is downregulated in some aggressive cancers; thus, molecules that promote tubulin tyrosination—perhaps TTCP inhibitors—may be useful chemotherapeutic agents for these cancers, which currently have poor prognosis.

Previously, in vitro use of purified TTL, tubulin and formyltyrosine was published in 2010, and showed that the reaction between the labeled tubulin and a novel hydrazine fluorophore can take place in a live cell. Abhijit Banerjee, Timothy D. Panosian, Kamalika Mukherjee, Rudravajhala Ravindra, Susannah Gal, Dan L. Sackett, and Susan Bane, "Site-Specific Orthogonal Labeling of the Carboxy Terminus of α-Tubulin", ACS Chemical Biology. Vol. 5 No. 8, pp 777-785 (2010), expressly incorporated herein by reference.

American Society for Cell Biology December 2012 meeting Poster #268 described in detail a cytostatic effect of formyltyrosine on cell growth. American Society for Cell Biology December 2012 meeting Poster #285 showed that use of formyltyrosine followed by a fluorescent dye results in fluorescently labeled microtubules that can be seen by fluorescence microscopy. Poster #2540 entitled "Labeling Tubulin with Fluorescent Probes in Live Cells" discusses 3fY tagging of tubulin followed by fluorescent labeling of live cells.

The only other method to fluorescently label microtubules in live cells (without genetic manipulation such as Green Fluorescent Protein) is to use fluorescent Taxol. Invitrogen sells two cell-permeable versions of this molecule. However, Taxol greatly affects the microtubules (increased stable polymer). The cells with fluorescently labeled tubulin using the present method are healthy for at least 24 hours after the labeling procedure.

The labeling reaction involves a chemical reaction that occurs between the labeled tubulin and the fluorophore (hydrazine, hydrazide or aromatic aldehyde). This reaction is unexpectedly very fast in PC3 cells. It is well known that the optimal pH for these reactions is around 4, and that the rate of the coupling reaction decreases dramatically above this pH. For this reason, most recent reactions are performed using a catalyst, generally 100 mM aniline. However, this was found to be unsatisfactory for tubulin, and 4-aminophenylalanine may be used as an alternative. This is detailed in Adam R. Blanden, Kamalika Mukherjee, Ozlem Dilek, Maura Loew, and Susan L. Bane, "4-Aminophenylalanine as a Biocompatible Nucleophilic Catalyst for Hydrazone Ligations at Low Temperature and Neutral pH", Bioconjugate Chem. 2011, 22, 1954-1961, expressly incorporated herein by reference.

It is also well known that sterics and electronic properties of the electrophile and nucleophile are critical to the kinetics of the covalent bond formation as well as the stability of the resulting bond. Jeet Kalia. Ronald T. Raines, "Advances in Bioconjugation", Curr Org Chem. 2010 January; 14(2): 138-147, expressly incorporated herein by reference. Thus, reactions performed with this system in biological systems invariably use an aromatic amine catalyst or a low pH and typically multiple hours of reaction time. Based on the chemistry of the functional groups, the reactions should take a long time and/or a catalyst and require large excess of fluorophore. See, e.g., Josep Rayo, Neri Amara, Pnina Krief, and Michael M. Meijler, "Live Cell Labeling of Native Intracellular Bacterial Receptors Using Aniline-Catalyzed Oxime Ligation", J. Am. Chem. Soc. 2011, 133, 7469-7475, expressly incorporated herein by reference. In contrast, labeling occurs within minutes when the fluorophore is added to the cells. Further, the present technology does not use such a large excess of ligand, so background is not a significant issue. Contrast with, Zhiwen Zhang, Brian A. C. Smith, Lei Wang, Ansgar Brock, Charles Cho, and Peter G. Schultz, "A New Strategy for the Site-Specific Modification of Proteins in Vivo", Biochemistry 2003, 42, 6735-6746, expressly incorporated herein by reference. A final dye concentration of 1 mM was employed, with extensive washing following an overnight staining, and works well for staining membrane bound proteins but results in a high background staining for cytosolic proteins.

In addition to tyrosine ligation, tubulin also undergoes posttranslational polyglutamylation of some of the glutamic acid residues in the carboxy terminus of both alpha and beta subunits. See, Carsten Janke and Jeannette Chloe Bulinski, "Post-translational regulation of the microtubule cytoskeleton: mechanisms and functions", Molecular Cell Biology, Vo. 12 2011 1773-1786; Edde, B; Rossier, J; Lecaer, J P; et al., "Posttranslational Glutamylation Of Alpha-Tubulin", Science Vol. 247 No. 4938 Pages 83-85 (1990), each of which is expressly incorporated herein by reference. The enzymes that do this are like tubulin tyrosine ligase. Janke, C; Rogowski, K; Wloga, D; et al., "Tubulin polyglutamylase enzymes are members of the TTL domain protein family", Science Vol. 308 No. 5729 Pages: 1758-1762 2005. Tubulin tyrosine ligase accepts as a substrate a tyrosine derivative in which the carboxylic acid is a hydrazide.

Tubulin polyglutamylases are therefore possible targets for glutamic acid hydrazides, e.g., alpha-hydrazide.

Other proteins undergo glutamylation. It may be possible to probe for this with a hydrazide derivative of glutamic acid. See, J. van Dijk, J. Miro, J.-M. Strub, B. Lacroix, A. van Dorsselaer, B. Eddé, C. Janke, "Polyglutamylation Is a Post-translational Modification with a Broad Range of Substrates", J. Biol. Chem., 283 (2008), pp. 3915-3922. Besides tubulins, nucleosome assembly proteins NAP1 and NAP2 have been shown to be polyglutamylated. However, using a proteomic approach, a large number of putative substrates for polyglutamylation in HeLa cells were identified, which serve as in vitro substrates for two polyglutamylases, TTLL4 and TTLL5. Tubulin in cilia also undergoes polyglycylation. See, Ikegami, Koji; Setou, Mitsutoshi, "Unique Post-Translational Modifications in Specialized Microtubule Architecture", Cell Structure and Function, Vol. 35 No. 1, Pages: 15-22 (2010); C. Regnard, E. Desbruyeres, J. C. Huet, C. Beauvallet, J. C. Pernollet, B. Eddé, "Polyglutamylation of nucleosome assembly proteins", J. Biol. Chem., 275 (2000), pp. 15969-15976, each of which is expressly incorporated herein by reference; this may be probed by hydrazide.

Otherwise unknown posttranslational modification with amino acids may be found. See, George A. Khoury, Richard C. Baliban, & Christodoulos A. Floudas, "Proteome-wide post-translational modification statistics: frequency analysis and curation of the swiss-prot database", Scientific Reports 1, 90 doi:10.1038/srep00090 (2011). See also Woodsmith J, Kamburov A, Stelzl U, "Dual Coordination of Post Translational Modifications in Human Protein Networks". PLoS Comput Biol 9(3): e1002933. doi:10.1371/journal.pcbi.1002933 (2013), each of which is expressly incorporated herein by reference.

Ikeda-Boku A, Ohno S, Hibino Y, Yokogawa T, Hayashi N, Nishikawa K, "A simple system for expression of proteins containing 3-azidotyrosine at a pre-determined site in *Escherichia coli*", J Biochem. 2013 March; 153(3):317-26. doi: 10.1093/jb/mvs153. Epub 2013 Jan. 10, expressly incorporated herein by reference, discloses an example of the "unnatural amino acid" technology that could be used to put unnatural amino acids such as 3-formyltyrosine or 3-acetyltyrosine into any protein.

Typically, the reaction between the nucleophile and electrophile would be expected to be slow. Jun Y. Axupa, Krishna M. Bajjuric, Melissa Ritland, Benjamin M. Hutchins, Chan Hyuk Kim, Stephanie A. Kazane, Rajkumar Halder, Jane S. Forsyth, Antonio F. Santidrian, Karin Stafin, Yingchun Lu, Hon Tran, Aaron J. Seller, Sandra L. Biroc, Aga Szydlik, Jason K. Pinkstaff, Feng Tian, Subhash C. Sinha, Brunhilde Felding-Habermann, Vaughn V. Smider, and Peter G. Schultza, "Synthesis of site-specific antibody-drug conjugates using unnatural amino acids", PNAS, Oct. 2, 2012, vol. 109, no. 40, pp. 16101-16106, expressly incorporated herein by reference, teach that the coupling reaction takes 4 days.

Kazane S A, Sok D, Cho E H, Uson M L, Kuhn P, Schultz P G, Smider V V, "Site-specific DNA-antibody conjugates for specific and sensitive immuno-PCR", Proc Natl Acad Sci USA. 2012 Mar. 6; 109(10):3731-6. doi: 10.1073/pnas.1120682109. Epub 2012 Feb. 15, expressly incorporated herein by reference, teaches coupling conditions which employ a pH of 4.5 and 100 mM methoxyaniline.

Rayo J, Amara N, Krief P, Meijler M M, "Live cell labeling of native intracellular bacterial receptors using aniline-catalyzed oxime ligation", J Am Chem Soc. 2011 May 18; 133(19):7469-75. doi: 10.1021/ja200455d. Epub 2011 Apr. 22, expressly incorporated herein by reference, employs an aniline catalyzed oxime formation in a live bacterial cell system. In this system, aniline (1 mM) catalyzes the reaction between aldehydes and oxyamines at neutral pH, resulting in oxime formation with good reaction rates, with labeling occurring over a period of 12 hours.

Rashidian M, Song J M, Pricer R E, Distefano M D, "Chemoenzymatic reversible immobilization and labeling of proteins without prior purification", J Am Chem Soc. 2012 May 23; 134(20):8455-67. doi: 10.1021/ja211308s. Epub 2012 May 8, expressly incorporated herein by reference, provides a reaction which was initiated by adding 100 mM aniline and allowed to proceed for 1 h at room temperature.

Yao J Z, Uttamapinant C, Poloukhtine A, Baskin J M, Codelli J A, Sletten E M, Bertozzi C R, Popik V V, Ting A Y, "Fluorophore targeting to cellular proteins via enzyme-mediated azide ligation and strain-promoted cycloaddition", J Am Chem Soc. 2012 Feb. 29; 134(8):3720-8. doi: 10.1021/ja208090p. Epub 2012 Feb. 14, expressly incorporated herein by reference, employs a 10 minute incubation followed by an extensive 2 hours of washing to remove excess fluorophore prior to imaging.

Georg C Rudolf, Wolfgang Heydenreuter and Stephan A Sieber, "Chemical proteomics: ligation and cleavage of protein modifications", Current Opinion in Chemical Biology 2013, 17:110-117, expressly incorporated herein by reference, discusses the attachment of molecular modifications onto proteins for various applications. However, no hydrazine/aldehyde couplings are mentioned in this review.

See also, Paresh Agarwala, Joep van der Weijdena, Ellen M. Slettena, David Rabukab, and Carolyn R. Bertozzi, "A Pictet-Spengler ligation for protein chemical modification", PNAS Jan. 2, 2013, vol. 110, no. 1, pp. 46-51 www.pnas.org/cgi/doi/10.1073/pnas.1213186110; See, Kathrin Lang, Lloyd Davis, Jessica Torres-Kolbus, Chungjung Chou, Alexander Deiters, and Jason W. Chin, "Genetically encoded norbornene directs site-specific cellular protein labelling via a rapid bioorthogonal reaction", Nature Chemistry Vol. 4 (2012) pp. 298-304; Arshad Desai and Timothy J. Mitchison, "Microtubule Polymerization Dynamics", Annu. Rev. Cell Dev. Biol. 1997. 13:83-117; Goodson, Holly V, "Generation of stable cell lines expressing GFP-tubulin and photoactivatable-GFP—tubulin and characterization of clones", Cold Spring Harbor protocols, Vol. 2010 Issue 9, Pages: pdb.prot5480; Sohye Jang, Kalme Sachin, Hui-jeong Lee, Dong Wook Kim, and Hyun Soo Lee, "Development of a Simple Method for Protein Conjugation by Copper-Free Click Reaction and Its Application to Antibody-Free Western Blot Analysis", Bioconjugate Chem. 2012, 23, 2256-2261; and Moritz J. Schmidt and Daniel Summerer, "A need for speed; genetic encoding of rapid cycloaddition chemistries for protein labelling in living cells", Chembiochem; a European journal of chemical biology, Vol. 13 Issue 11 (2012), pp. 1553-1557, each of which is expressly incorporated herein by reference.

Methods available for microtubule labeling and associated disadvantages

| Methods | Disadvantage |
| --- | --- |
| 1 Recombinant protein expression (GFP/RFP tubulin) | GFP is a 27 kD protein (vs tubulin, which is 2 50 kD monomers) Only 3% of tubulin is labeled-cells not viable with higher labeling Requires genetic manipulation |
| 2 Use of drugs conjugated with probes Example: BODIPY FL Vinblastine (Invitrogen) Vinblastine 4'-anthranilate (Invitrogen) TubulinTracker Green reagent (Invitrogen) Oregon Green 488 paclitaxel bis-acetate (Invitrogen) | Interferes with microtubule dynamics Example: Vinblastine inhibits tubulin polymerization Taxol promotes tubulin polymerization |
| 3 Microinjection | Single cell manipulation Tedious process |
| 4 Other probes for tubulin Example: DCVJ (4-(dicyanovinyl) julolidine(Invitrogen) | Non-specific—useful with pure protein only Example: DCVJ (4-(dicyanovinyl)julolidine: Also binds to bovine brain calmodulin |
| 5 GTP analog modified with TAMRA, Cy3, or Cy5 (BioTechniques 50:43-48 Jul. 2011) | Non-specific—useful with pure protein only |

SUMMARY

Microtubules are part of the cytoskeleton in all human cells. These structures grow and shrink in size in response to the needs of the cell. One enzyme involved in this process is tubulin tyrosine ligase. Many cancer cells are deficient in this enzyme, and it is possible that loss of this enzyme's activity is associated with particularly aggressive cancer.

Observation of microtubule dynamics in live cells using fluorescence microscopy is of critical importance in studying cytoskeleton biology. Current methods used for such studies rely on expression of tubulin fused with a fluorescent protein (46), introducing exogenously labeled tubulin (47), or using fluorescently labeled microtubule binders such as taxol (48). A technique was developed to visualize microtubules in live cells that does not require genetic manipulation or microinjection. Moreover, this method also avoids perturbation of the endogenous microtubule network that occurs with taxol treatment. This technique exploits tyrosination and detyrosination of tubulin (49), a posttranslational modification cycle specific to the C-terminus of α-tubulin. Specifically, cells are grown in medium supplemented with a tyrosine derivative possessing a reactive functional group. The cellular enzyme tubulin tyrosine ligase attaches the unnatural amino acid to a single site on tubulin. After removal of excess unnatural amino acid, addition of fresh media containing a suitably derivatized fluorophore yields fluorescent tubulin, which incorporate into cellular microtubules. Importantly, 24 h treatment with the unnatural amino acid followed by treatment with a fluorophore does not alter microtubule network or cell morphology. An efficient labeling technique is provided that can assist in localization and visualization of this cytoskeletal protein. Similar approach may also be suitable for site-specific fluorescent labeling of other proteins in cellular milieu.

Currently available methods for labeling tubulin in live cells involve recombinant protein expression, microinjection or the use of taxol-linked probes. The present technology provides a technique that can be employed to visualize microtubules in live cells without genetic manipulation or perturbing the protein function. Specifically, this technique exploits the mechanism of tyrosination/detyrosination cycle, a posttranslational modification specific to the C-terminus of α-tubulin, to covalently attach a chemical probe to it. Cells are first grown in medium supplemented with a bioorthogonal amino acid, such as 3-formyltyrosine (3fY), 3-acetyl tyrosine or tyrosine hydrazide. These un-natural amino acids readily enter the cell and can be appended to the C-terminus of α-tubulin by endogenous tubulin tyrosine ligase, but are not generally incorporated into proteins produced by the normal protein synthesis mechanisms, thus providing specificity based on the post-translational modification enzymes. Cells are subsequently treated with a suitably derivatized fluorophore that reacts specifically with a reactive chemical site on the bioorthoginal amino acid.

Covalent bond formation between the protein bound aldehyde of 3-formyl tyrosine, the acetyl of 3-acetyl tyrosine, or the hydrazide functionality of tyrosine hydrazide and the corresponding reactive fluorophore takes place within a short period in the intracellular milieu. With certain fluorophores, this reaction is accompanied by an increase in fluorescence that makes this highly dynamic protein suitable for visualization. Interestingly, 24 hour treatment with 3fY, 3-AcY or Y-azide followed by treatment with a fluorophore does not alter the microtubule network or cell morphology.

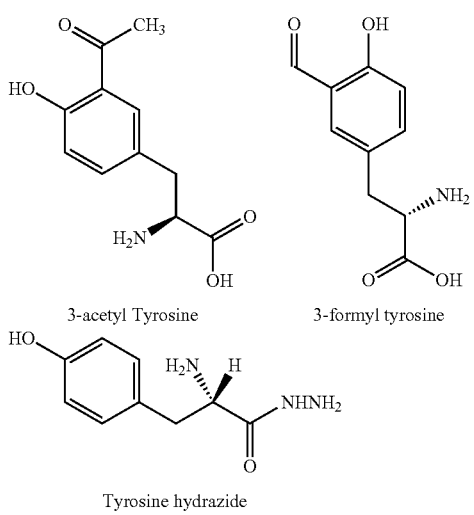

3-acetyl Tyrosine    3-formyl tyrosine

Tyrosine hydrazide

A unique feature of some of these probes is that they are weakly fluorescent until they react with the modified amino acid, therefore yielding negligible background fluorescence from unreacted fluorophore. Both the enzymatic reaction and the chemical coupling are designed to take place in live cells; thus, tubulin tyrosination in live cells may be observed both temporarily and spatially. By attaching appropriate probes directly to a defined site on polymerized tubulin, superior ultra high resolution images of microtubules using sub-diffraction microscopy techniques are attainable.

Spectroscopic probes suitable for assessing dynamic properties of the carboxy terminus of tubulin are provided that minimally perturb the peptide structure. Since native mammalian tubulin is very difficult to express in E. coli (17), molecular biology techniques will not produce quantities required for in vitro experiments. The size of the probe is important, because even a small peptide appended to a carboxy terminus can affect the cellular function of tubulin (18).

The present approach takes advantage of the high target specificity of TTL to attach a modified tyrosine residue to α-tubulin. The tyrosine derivative possesses a reactive functional group that is orthogonal to the endogenous amino acids. The modified protein can then be reacted with a probe that contains a complementary and specific reactive group. The process is both specific and versatile, that is, a single site on the protein will be covalently labeled, but the nature of the fluorophore (or alternate probe) can be varied. One enzymatic reaction can form the basis for multiple labels.

For 3fY and Y-azide, the chemistry is the well-known reaction of hydrazone formation. The properties of both the carbonyl and the hydrazine reagents were carefully considered. Purified tubulin is notoriously sensitive to changes in pH and temperature (19), so it is important that the labeling reaction be accomplished as rapidly as possible, near neutral pH and at temperature of 37° C. or less. The strategies form the basis of a broadly applicable approach for site specific labeling of a protein with a wide variety of probes. That is, the technology would generally act similarly for labeling a macromolecule that is subject to a specific post-translational modification, by an enzyme that accepts as a substrate a bioorthogonal substrate, to form an adduct that reacts in vivo with a corresponding label, such as a derivatized fluorophore.

The ability to label microtubules in live cells permits study of microtubule dynamics, permits formulation of potential chemotherapeutics, and assist in determining a mechanism of microtubule drug action. Microtubules are commonly used to visualize relative location of other cellular structures of interest. Fluorophore labeling of microtubules also permits superresolution microscopy.

The present technology therefore provides the following advantages: (1) No genetic manipulation involved. It can theoretically be done on any cell. (2) Site-specific labeling. Bioorthogonal chemistry is used. (3) Less labor intensive than prior methods. Also, one procedure is employed for any fluorophore (which is not true for fluorescent proteins). (4) Cell morphology, microtubule network and cell viability remains unaltered (for 24 hours). (5) Commercially available fluorescent probes can be used for labeling 3-formyltyrosine and 3-acetyltyrosine (Invitrogen). Wide range of excitation/emission range available.

The unnatural amino acids, 3-formyltyrosine and 3-acetyltyrosine are not commercially available. However, tyrosine hydrazide is commercially available. The rosamine aldehyde fluorophore used for tyrosine hydrazide labeling not commercially available. However, other aldehyde-containing fluorophores are synthetically accessible and commercially available. Various rosamine derivatives, and methods of preparation are disclosed in WO 2010/033011, expressly incorporated herein by reference.

See. Liangxing Wu and Kevin Burgess, "Synthesis and Spectroscopic Properties of Rosamines with Cyclic Amine Substituents", J. Org. Chem. 2008, 73, 8711-8718, and Liangxing Wu, "Design, Syntheses and Applications of Fluorescent Dyes", Doctoral Dissertation, Texas A&M University (2009), each of which is expressly incorporated herein by reference.

Tyrosine derivatives containing a reactive functional group (aldehyde, acetyl, or hydrazide) are substrates for the enzyme tubulin tyrosine ligase in live cells. These unnatural amino acids are apparently incorporated into a single protein at a single site—C-terminus of the alpha subunit of tubulin. No other instances when any of these three unnatural amino acids have been used for protein labeling under any circumstances have been found.

It is therefore an object to provide a method for labeling microtubules in living cells, comprising incubating the living cells with 3-acetyl tyrosine for a sufficient time for the 3-acetyl tyrosine to be ligated to alpha tubulin by tubulin tyrosine ligase, and then adding a cell membrane permeable label having a hydrazine or hydrazide functional group, wherein the hydrazine or hydrazide of the label spontaneously reacts with the ketone of the 3-acetyl tyrosine to form a hydrazone covalent bond. The cell membrane permeable label having a hydrazide functional group may be coumarin hydrazine. The coumarin hydrazine may be 7-hydrazino-4-methyl coumarin. The label preferably spontaneously reacts with the ketone of the 3-acetyl tyrosine to form a hydrazone covalent bond substantially without toxicity to the living cells. The label may comprise a fluorescent probe. The method may further comprise acquiring a fluorescent image of the label showing the microtubules.

It is a further object to provide a method for labeling microtubules in living cells, comprising incubating the living cells tyrosine hydrazide for a sufficient time for the tyrosine hydrazide to be ligated to alpha tubulin by tubulin tyrosine ligase, and then adding a cell membrane permeable label having an aldehyde or ketone functional group, wherein the hydrazide of the tyrosine hydrazide spontaneously reacts with the aldehyde or ketone of the label to form a covalent bond. The label preferably spontaneously reacts with the hydrazide functionality of the tyrosine hydrazide form a covalent bond substantially without toxicity to the living cells. The label may be a fluorescent probe. The method may further comprise acquiring a fluorescent image of the label showing the microtubules.

The cell membrane permeable label having an aldehyde or ketone functional group may comprise a rosamine aldehyde. The rosamine aldehyde is, for example, (1-(9-(4-formylphenyl)-6-(pyrrolidin-1-yl)-3H-xanthen-3-ylidene) pyrrolidine or its HCl salt: (1-(9-(4-formylphenyl)-6-(pyrrolidin-1-yl)-3H-xanthen-3-ylidene)pyrrolidinium chloride). More generally, the rosamine aldehyde comprises a composition having formula I:

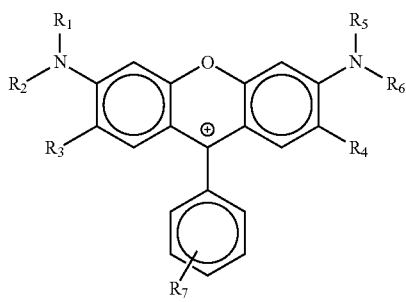

wherein $R_7$ is an alkyl or aryl comprising an aromatic aldehyde moiety;

$R_3$ and $R_4$ are the same or different selected from the group consisting of hydrogen, substituted or unsubstituted alkyl, aryl, heteroalkyl, heteroaryl, haloalkyl, and haloaryl, $R_1$ and $R_2$, and $R_5$ and $R_6$, are the same or different or $R_1$ and $R_2$, or $R_5$ and $R_6$ together form a ring having at least 5 members, selected from the group consisting of substituted or unsubstituted alkyl, aryl, heteroalkyl, heteroaryl, haloalkyl, and haloaryl, wherein the rosamine aldehyde is at least one of soluble in water or lipid membranes.

$R_1$ and $R_2$, and $R_5$ and $R_6$ may together be pyrrolidine.

$R_7$ may be 4-formylphenyl.

According to one set of embodiments, the rosamine aldehyde is water soluble, $R_3$ and $R_3$ are hydrogen, $R_7$ is 4-formylphenyl, and $R_1$ and $R_2$ together and $R_5$ and $R_6$ together, are each:

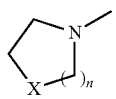

wherein N is shown in formula 1, X is $CH_2$, O or NR, n is 1 or 2, and R is hydrogen, substituted or unsubstituted alkyl, aryl, heteroalkyl, heteroaryl, haloalkyl, and haloaryl.

According to another set of embodiments, a rosamine aldehyde is provided comprising a composition having formula I:

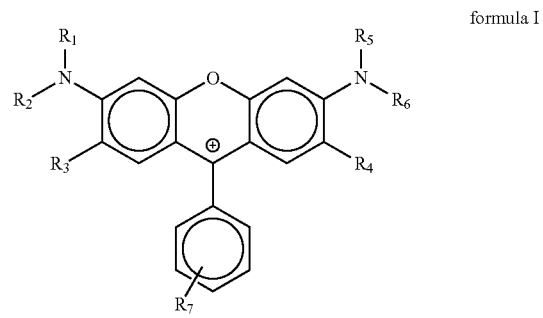

wherein $R^7$ is an alkyl or aryl comprising an aldehyde moiety;

$R_3$ and $R_4$ are the same or different selected from the group consisting of hydrogen, substituted or unsubstituted alkyl, aryl, heteroalkyl, heteroaryl, haloalkyl, and haloaryl, $R_1$ and $R_2$, and $R_5$ and $R_6$, are the same or different or $R_1$ and $R_2$, or $R_5$ and $R_6$ together form a ring having at least 5 members, selected from the group consisting of substituted or unsubstituted alkyl, aryl, heteroalkyl, heteroaryl, haloalkyl, and haloaryl, wherein the rosamine aldehyde is at least one of soluble in water or lipid membranes.

The rosamine aldehyde preferably has formula II:

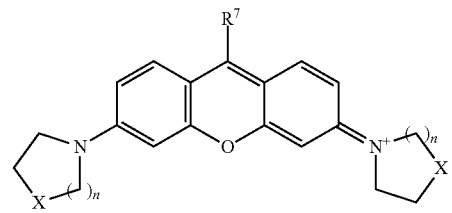

$R^7$ is an aromatic or aromaticlaly conjugated aldehyde, wherein X is O, S, $CH_2$, $CHR^8$, $CR^8R^9$ or $NR^8$, n is 1 or 2, and $R^8$ and $R^9$ are each the same or different, selected from the group consisting of hydrogen, substituted or unsubstituted alkyl, aryl, heteroalkyl, heteroaryl, haloalkyl, and haloaryl.

wherein the rosamine aldehyde is water soluble, substantially non-toxic to living cells at a concentration of less than about 100 µM.

More preferably, X is $CH_2$, n is 1, and $R^7$ is formylphenyl. The Rosamine aldehyde may therefore comprise (1-(9-(4-formylphenyl)-6-(pyrrolidin-1-yl)-3H-xanthen-3-ylidene) pyrrolidine or its HCl salt: (1-(9-(4-formylphenyl)-6-(pyrrolidin-1-yl)-3H-xanthen-3-ylidene)pyrrolidinium chloride).

Results and Discussion

Tubulin Tyrosine Ligase: Substrate Specificity. The only cellular substrate that has been identified for TTL is the C-terminus of α-tubulin that terminates in the sequence Glu-Glu (8). The enzyme accepts some variation in the structure of the amino acid substrate, although the efficiency of incorporation is usually substantially lower than that for the normal L-tyrosine substrate.

There does not appear to be enough flexibility in the structure of the substrate to attach a fluorescent amino acid such as a dansyl or coumarin derivative using the enzyme (20, 21). Aromatic amino acids with minor structural differences such as L-phenylalanine, 3-iodotyrosine, 3-azidotyrosine, and 3-fluorotyrosine are weak substrates for TTL and are inhibitors of the enzyme (22-25). The unnatural amino acid 3-nitrotyrosine can also be incorporated into tubulin by the isolated human enzyme and in live cells (26-28).

Inhibition of [3H]-L-tyrosine incorporation into tubulin by TTL was measured for several aromatic amino acid derivatives to evaluate their potential as substrates for the enzyme (Table 1). Replacing the 4-hydroxyl group with an amine produced no inhibition of TTL at millimolar concentrations; thus, subsequent amino acids tested retained the 4-hydroxyl functionality. The 3-substituted derivatives tested inhibited [3H]L-tyrosine incorporation into tubulin at low millimolar concentrations. Two tyrosine derivatives possessing functional groups with orthogonal reactivity were evaluated in this assay.

TABLE 1

Inhibition of tubulin tyrosine ligase by tyrosine derivative

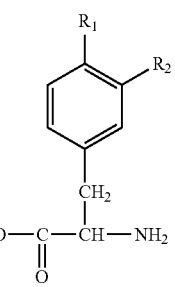

| L-Amino Acid | Structure | $K_i$, mM |
| --- | --- | --- |
| Tyrosine | $R_1$ = OH, $R_2$ = H | 0.025 |
| 3-Nitrotyrosine | $R_1$ = OH, $R_2$ = $NO_2$ | 0.4 |
| 3-Aminotyrosine | $R_1$ = OH, $R_2$ = $NH_2$ | 0.2 |
| 3-Azidotyrosine | $R_1$ = OH, $R_2$ = $N_3$ | 0.2 |
| 3-Formyltyrosine | $R_1$ = OH, $R_2$ = CHO | 0.3 |
| 4-Aminophenylalanine | $R_1$ = $NH_2$, $R_2$ = H | >4 |

Both 3-azidotyrosine and 3-formyltyrosine inhibited the enzyme to approximately the same extent as 3-nitrotyrosine. Since 3-nitrotyrosine is a substrate for TTL and has been successfully incorporated into α-tubulin in cultured cells (11), both of these amino acids should be potential chemical labels for tubulin in cells as well as for purified tubulin through TTL.

Orthogonal labeling of tubulin using 3-azidotyrosine should be accessible through 1,3-dipolar reaction with an alkyne-containing label (29). Unless the alkyne is strained, however, the reaction requires copper(I) ion (30), and it is unlikely that tubulin will retain assembly activity after exposure to copper ion (31). Focus was therefore placed on labeling tubulin with the aromatic aldehyde 3-formyltyrosine.

Removal and replacement of the C-terminal tyrosine of α-tubulin can be assessed by Western blot. The antibody TUB-1A2 is specific for α-tubulin possessing a C-terminal tyrosine but does not recognize detyrosinated tubulin (32). FIG. 1 shows that removal of the C-terminal tyrosine of bovine brain α-tubulin abolishes the antibody binding to the protein, while retyrosination with TTL restores it. Tubulin that has been treated with 3-formyltyrosine in the presence of TTL can be observed in the Western blot, indicating that the antibody is also able to recognize the formylated C-terminus. The presence of a carbonyl in α-tubulin was con-firmed reacting the protein with dinitrophenylhydrazine (DNPH) followed L-tyrosine or 3-formyltyrosine as described under Methods and then subjected to SDS-PAGE. Top: Western blot with tyrosinated α-tubulin antibody (Sigma-Aldrich TUB-1A2). Bottom: Coomassie stain. Lane 1: Tubulin. Lane 2: Tubulin treated with CPA. Lane 3: CPA-treated tubulin retyrosinated with tyrosine. Lane 4: CPA-treated tubulin retyrosinated with 3-formyltyrosine. The mass of protein loaded each well was 0.66 μg for the Western blot and 10 μg for the protein stain. Hydrazone Formation: Effect of the Structure of the Nucleophile. Reactions of aldehydes and ketones with hydrazines, hydroxylamines, and amines have been extensively studied (33). The rate vs pH curve is bellshaped; the maximum reaction rate is around the pKa of the hydrazine. Phenyl hydrazide has a pKa of 3.1, 4 log units away from the desired reaction pH, while phenyl hydrazine has a pKa of 5.3 (34). This feature is significant for bioorthogonal labeling under physiological conditions. Almost all of the commercially available fluorophores for fluorescent labeling of aldehydes and ketones are hydrazides, which are poorly reactive at neutral pH. A fluorophore was hypothesized possessing a hydrazine functional group would react more quickly at neutral pH. An aromatic hydrazine coumarin derivative was therefore synthesized. The compound 7-hydrazino-4-methyl coumarin (coumarin hydrazine, FIG. 2) was allowed to react with 3-formyltyrosine, and the kinetics of hydrazone formation were followed by absorption difference spectroscopy. Hydrazone formation is complete within 120 min under these conditions: the second-order rate constant is 53 $M^{-1}$ $min^{-1}$ (FIG. 3, panel A). Under the same conditions, reaction of the commercially available coumarin hydrazide (FIG. 2) was barely detectable after 4 h. The second order rate constant for this reaction was estimated to be less than 2 $M^{-1}$ $min^{-1}$.

It should be possible to increase the reaction rate of hydrazone formation using aniline as a catalyst, as shown by Dirksen and Dawson (35). In the absence of such a catalyst, though, it is clear that an aromatic hydrazine and not a hydrazide is better suited for the tubulin labeling reaction. There are other reasons why an aromatic hydrazine is a good choice for the nucleophile. Hydrazones formed from aromatic hydrazines are more stable than those formed from aliphatic hydrazines, which are in turn more stable than those formed from hydrazides (34).

Another important feature of a hydrazine reactive group is the possibility that hydrazone formation may alter the electronic properties of the fluorophore. For example, if the hydrazino functional group is directly bonded to the chromophore, formation of the hydrazone may provide conjugation between the aromatic aldehyde and the fluorescent hydrazine. Covalent bond formation may shift the absorption and emission maxima of some fluorophores to longer wavelengths than the corresponding hydrazine (36). In addition, fluorophores possessing aromatic amines are frequently weakly fluorescent, often as a result of intramolecular photoelectron transfer involving the amine lone pair. Structural modifications that delocalize the electron density on the amine nitrogen, such as amide bond formation, can greatly increase the quantum yield of the fluorophore (37). It is therefore possible that feebly fluorescent hydrazines may become highly fluorescent species upon hydrazone formation, that is, hydrazone formation may "turn on" the fluorophore (38). Thus, covalently bound fluorophore may be readily detectable in the presence of noncovalently bound fluorophore.

To test this hypothesis, the absorption and fluorescence spectra of coumarin hydrazine and the salicylaldehyde hydrazone of coumarin hydrazine were measured, which serves as a model compound for the protein-bound hydrazone. Hydrazone formation causes a shift in both the absorption and emission maxima of coumarin hydrazine and a significant increase in quantum yield (Table 2). Thus, as a result of the difference in the spectroscopic window and the quantum yields of coumarin hydrazine and its salicylaldehyde hydrazone, fluorescence from unreacted coumarin hydrazine can be averted.

Orthogonal Labeling of Native Tubulin. FIG. 3, panel B shows that coumarin hydrazine reacts with 3-formyltyrosinated tubulin to form a fluorescent product. Its emission maximum is red-shifted relative to tubulin, which corresponds to α-tubulin. No fluorescence is observed in the control samples. Limited proteolysis with subtilisin caused a time-dependent decrease in the fluorescence intensity of the α-tubulin band, which is consistent with the idea that the fluorophore is attached to the C-terminus of α-tubulin (39). The fluorescently labeled tubulin retains its ability to polymerize, which is illustrated for bovine brain tubulin in FIG. 5.

TABLE 2

Absorption and emission maxima and quantum yield of coumarin hydrazine and its cylaldehyde hydrazone in methanol at 25° C.

| fluorophore | Abs max, nm | Em max nm | φ |
|---|---|---|---|
| (coumarin-NHNH$_2$) | 360 | 432 | 0.046 |
| (coumarin-NHN=CH-C$_6$H$_4$-OH) | 380 | 459 | 0.131 |

Hydrazone Formation in Cells. Preliminary experiments to evaluate the suitability of the fluorophore for live cell imaging have been performed using PC3 cells. The fluorophore is quickly taken up by the cells and can be rapidly removed by washing. FIG. 6 shows cells that have been grown in tyrosine-depleted medium supplemented with either 50 µM L-tyrosine or 50 µM 3-formyltyrosine and then have been treated with 20 µM coumarin hydrazine. Images were obtained shortly after addition of the probe (15-20 min), which was not removed from the medium. Cells grown in 3-formyltyrosine are significantly brighter than those grown in L-tyrosine. Thus, the reaction between the un-natural amino acid and the hydrazine can occur in and can be observed in an intracellular environment.

Tubulin Labeling in Cells. This two-step labeling process can be used to fluorescently tag α-tubulin in live cells. An initial assessment has been performed using CHO cells. Cells grown in tyrosine-depleted medium were treated overnight with equal concentrations of either L-tyrosine or 3-formyltyrosine followed by a 2-h incubation with coumarin hydrazine. Proteins of the cell lysate were separated using SDS-PAGE. A single fluorescent protein was observed in the lysate, which was identified by Western blot to be α-tubulin (FIG. 7).

Conclusion. An in vitro system is provided for adding a 3-formyltyrosine residue to just the C-terminus of α-tubulin, which is highly specific both in purified protein and in cultured cells. The modified tyrosine, which remains a substrate for TTL, possesses a chemically reactive group that is orthogonal to the amino acid residues of the protein. This unnatural amino acid is capable of reacting with appropriately functionalized probes to form a covalent bond solely between the modified amino acid and the label. Covalent bond formation between the unnatural amino acid and the fluorophore can take place at moderate temperatures at neutral pH, which are conditions amenable to covalent bond formation in live cells.

Furthermore, the fluorescent probe prepared for this work provides additional proof in principle that a hydrazine bonded directly to a fluorophore π-system may alter the optical properties of a fluorophore upon hydrazone formation (36). The fluorophore is weakly fluorescent in a polar environment; covalent bond formation causes it to "turn on". Thus, owing to the shift in absorption and emission maxima in conjunction with an increase in the quantum yield, one may observe only those proteins that possess the appropriate reactive group in the presence of unreacted probe.

Aspects of this project should be applicable to other systems. For example, aromatic hydrazine-containing fluorophores that "turn on" when a hydrazone bond is formed may be useful for labeling other proteins containing aldehydes, such as cell surface glycoproteins (36). Ideally, the observation window for the fluorescently labeled protein can be changed simply by selecting a different reactive fluorophore for the experiment. This two step labeling system should be broadly applicable to site-specific labeling of proteins using unnatural amino acid mutagenesis methodology (40, 41). Methyl ketone derivatives of phenylalanine have already been developed for this purpose. Hydrazone formation with an o-hydroxy benzaldehyde moiety occurs more rapidly than with an unsubstituted aromatic ketone (42, 43). The 3-formyltyrosine could be considered as an alternative electrophile if a more reactive group is required for a particular application.

3-Acetyl Tyrosine is also a substrate for TTL and is incorporated into microtubules in live cells. It has an advantage in that it is less cytotoxic over 24 hour period than 3fY. The intracellular reaction appears a bit slower than with 3fY. It is generally unexpected that the hydrazide reaction occurs at all during the time of observation. Outside the cell, the reaction between the two components (fluorophore hydrazide and 3-acetyltyrosine) is so slow at pH 7 that the reaction is not useful for labeling (days vs. less than an hour in the cell). This difference may be due to micro-conditions within the cell, or as-yet unidentified catalytic components.

Tyrosine hydrazide (Yzide) may also be used as the bioorthogonal amino acid. The chemistry differs from 3fY, and thus different reactive pairs are employed. As such, this provides the opportunity for dual labeling of microtubules. Some data indicates that in some respects, a tyrosine hydrazide/fluorophore system is superior to the 3fY procedure. For example, no toxicity is observed with tyrosine hydrazide, and there is possibly better incorporation of Yzide into microtubule. This hydrazide/fluorophore makes less punctate structures. Punctate structures develop as a function of time. The incubation can be performed very quickly, so punctate structures are in general no longer an issue.

3-formyl tyrosine-fluorphore hydrazide coupling reaction

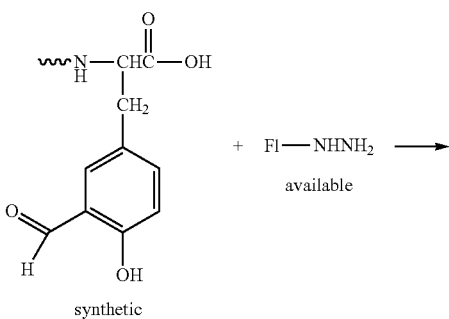

synthetic

Tyrosine hydrazide-fluorphore aldehyde coupling reaction

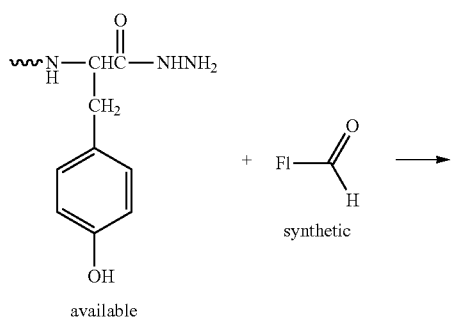

The bioorthogonal amino acids were found to have the following toxicities when cells were treated with the amino acid residues for 96 h before performing SRB assay:

Amino acid IC 50
3fY Amino acid 1>25 µM
AcY Amino acid 2>5 mM
Yzide Amino acid 3>5 mM (No toxicity observed with 5 mM ligand)

BRIEF DESCRIPTION OF THE FIGURES

FIGS. 6A-6D show that hydrazone formation occurs in live cells and is accompanied by an increase in probe fluorescence. PC3 cells were grown to 50% confluence in Ham's F-10 medium. The cells were incubated for 24 h with fresh medium supplemented with 50 µM L-tyrosine (FIGS. 6A and 6B) or 50 µM 3-formyltyrosine (FIGS. 6C and 6D). After the cells were washed with fresh medium, medium containing 20 µM coumarin hydrazine was added, and the cells were observed under laser scanning confocal microscope. FIGS. 6A and 6C: Fluorescence images using violet laser diode excitation (405 nm) and emission bandpass of 420-480 nm. FIGS. 6B and 6D: Differential interference contrast images.

FIG. 7A, Coumassie stain; FIG. 7B, Western blot of lystate using a polyclonal antibody to α-tubulin; FIG. 7C, Gel of the lysate visualized under long wavelength UV light (shown as brightfield).

FIG. 11 shows a composite, red channel and blue channel brightfield fluorescent micrograph images of the cells.

FIG. 13 shows a composite, red channel and blue channel brightfield fluorescent micrograph images of the cells.

METHODS

Figure 1:
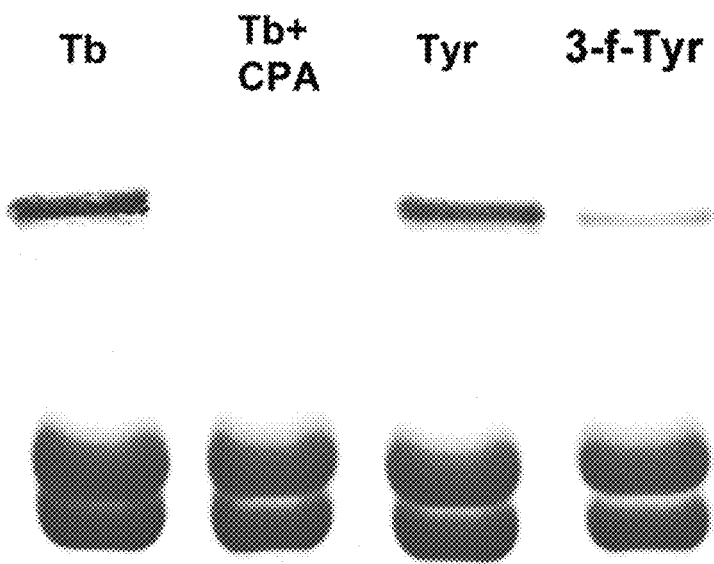
FIG. 1 shows 3-formyl tyrosine is incorporated into alpha-tubulin. Carboxypeptidase A (CPA) treated tubulin was incubated with tubulin tyrosine ligase in the presence of either tyrosine or 3-formyltyrosine. Tyrosination was detected by Western blot.

Synthesis. The unnatural amino acid 3-formyltyrosine was synthesized from BOC-L-tyrosine by the Reimer-Tiemann reaction followed by deprotection with trifluoro-acetic acid in dichloromethane. The fluorophore 7-hydrazino-4-methyl coumarin was synthesized from 7-amino-4-methyl coumarin by treatment with nitrous acid followed by $SnCl_2$. The salicylaldehyde hydrazone of coumarin hydrazine was prepared in ethanol with trifluoro-acetic acid catalysis.

Rosamine aldehyde, e.g., the HCl salt, (1-(9-(4-formyl-phenyl)-6-(pyrrolidin-1-yl)-3H-xanthen-3-ylidene)pyrrolidinium chloride), was prepared using methods similar to those disclosed in WO 2010/033011, expressly incorporated herein by reference. See also, U.S. Pat. Nos. 5,798,276; 5,846,737; 5,847,162; 6,017,712; 6,025,505; 6,080,852; 6,716,979; 6,562,632, expressly incorporated herein by reference.

Tubulin Tyrosine Ligase. An initial supply of TTL was a gift of Prof. Dr. Jürgen Wehland and Dr. Christian Erck (Gesellschaft für Biotechnologische Forschung, Germany) and was stored at −80° C. Human TTL was prepared using expression vector p Receiver 05x (Genecopoeia, Md.), transformed into the Escherichia coli expression strain BL21. Equivalent results were obtained with TTL from both sources.

Tubulin Preparation. Tubulin was isolated from bovine brain by two cycles of assembly/disassembly followed by phosphocellulose chromatography and was stored in liquid nitrogen until use (44). Tubulin was detyrosinated by combining 30 μM tubulin in PME buffer (0.1 M PIPES, 1 mM $MgSO_4$, 2 mM EGTA, pH 6.90) with 0.1 mg $mL^{-1}$ carboxypeptidase A (Sigma) and allowed to react 30 min at 37° C. The reaction was stopped by the addition of DTT to 20 mM. The cleaved tyrosine was removed, and buffer was exchanged by rapid gel filtration using Sephadex G-50 in PME buffer. Removal of the C-terminal tyrosine was confirmed by Western blot with the tyrosinated tubulin specific antibody TUB-1A2 (Sigma). Detyrosinated tubulin was drop frozen in liquid nitrogen and stored in liquid nitrogen until use. To retyrosinate tubulin with either L-tyrosine or 3-formyltyrosine, detyrosinated tubulin was thawed and equilibrated in TTL buffer using gel filtration chromatography (TTL buffer=25 mM MES, 150 mM KCl, 27 μM $MgCl_2$, 2.5 mM ATP, 1 mM DTT, 1.5% glycerol, pH 6.8). A final concentration of 10 μM tubulin was combined with 1 mM ligand (L-tyrosine or 3-formyltyrosine) and 0.1 mg $mL^{-1}$ TTL and allowed to react for 30 min at 37° C. Excess ligand was removed by rapid gel filtration into PME buffer. Control experiments in which TTL was excluded from the sample were also performed. The presence of a carbonyl in just the tubulin sample treated with TTL and 3-formyltyrosine was confirmed using the OxyBlot Protein Oxidation Detection Kit (Chemicon International).

[3H]-Tyr Incorporation Assay. TTL was thawed and diluted to 1 mg $mL^{-1}$ immediately before use. Detyrosinated tubulin (10 μM tubulin) in TTL buffer was combined with 0.007 μCu $μL^{-1}$ [3H-Tyr], 0.1 μg $μL^{-1}$ TTL, and various concentrations of inhibitor. The mixture was allowed to react for 30 min at 37° C. A 35 μL aliquot of the sample was placed onto DEAE chromatography paper (Whatman) and allowed to dry for 30 min. The protein was fixed using 200 μL of 10% acetic acid and allowed to dry for 10 min. Excess [3H-Tyr] was removed by 2 washes with 3.5 mL of 100% ethanol. The paper was allowed to dry for 30 min and then was combined with 10 mL of Scintiverse (BD) scintillation fluid. The amount of [3H]-tyrosine on each filter was determined using a β-counter.

Kinetic Measurements. Kinetics of hydrazone formation were measured using absorption difference spectroscopy. Dual chamber cells were loaded with identical volumes of 3-formyltyrosine (50 μM) and the selected nucleophile (coumarin hydrazine or coumarin hydrazide, 500 μM). The cell was placed in a thermostatted cell holder in an HP 8453 UV-vis spectrophotometer and equilibrated to 25° C. A baseline was established by blanking the instrument with the dual chamber cell. The solutions were mixed by rapid inversion of the cell (which doubles the path and halves the concentration of each component). Absorption difference spectra were collected as a function of time. The change in absorbance for one wavelength was selected from the spectral data, and these values were plotted as a function of time. The data were analyzed as a single pseudo-first-order reaction and were fit to the appropriate equation using SigmaPlot 10.0.

Figure 3:
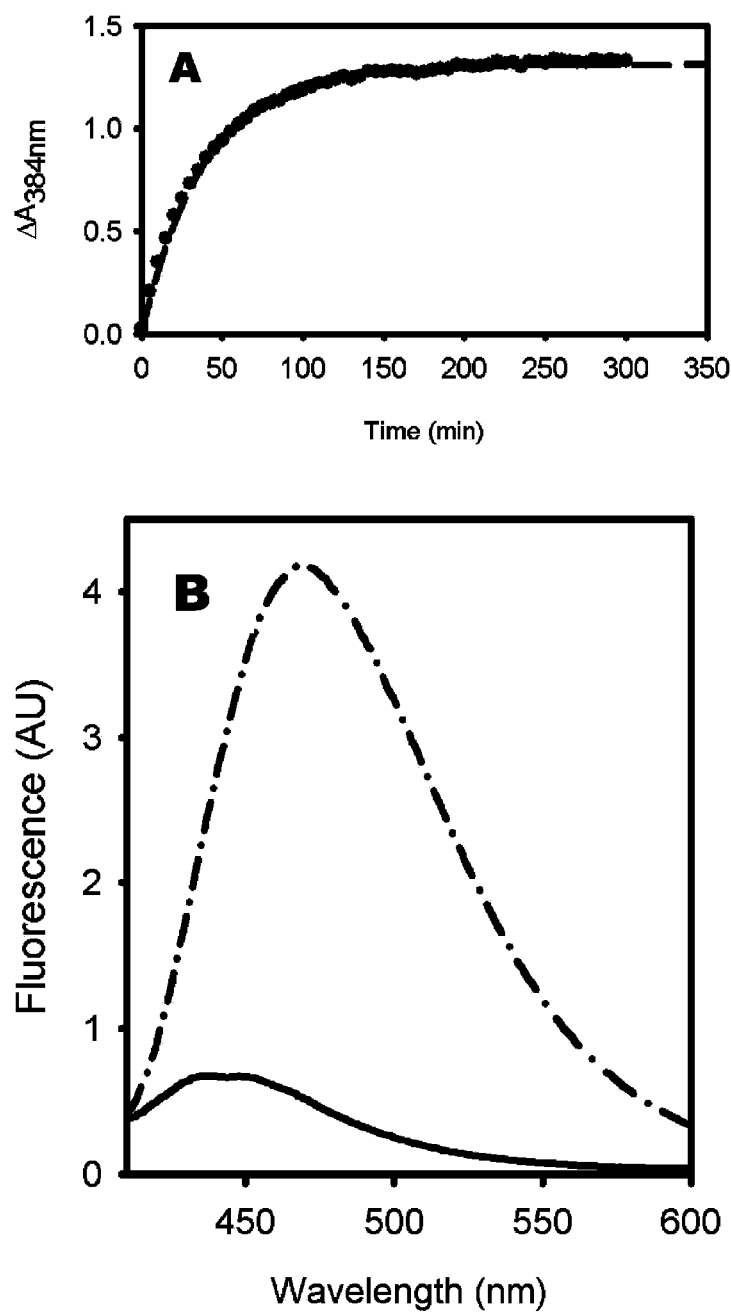
FIG. 3A shows kinetics of hydrazone formation between coumarin hydrazine and 3-formyltyrosine. Coumarin hydrazine (25 µM) was mixed with 3-formyltyrosine (250 µM) in PME buffer (pH 6.9) at 25° C. The absorption difference spectrum was collected at 5 min intervals and the change in absorption at 384 nm was plotted. Solid line: Fit of data to a single exponential.
FIG. 3B shows emission spectrum of fluorescently labeled tubulin. CPA-treated tubulin was retyrosinated with L-tyrosine (solid curve) or 3-formyltyrosine (dotdash curve) followed by treatment of coumarin hydrazine as described under Methods. Each sample contained 2 µM tubulin. The excitation wavelength was 392 nm.

Fluorecent Labeling of Tubulin with Coumarin Hydrazine. Coumarin hydrazine was freshly prepared by dissolving the solid material in PME buffer, which was then centrifuged to remove undissolved particles. The concentration of coumarin hydrazine was determined by absorption spectroscopy (using 8346 nm=1.9×104 $M^{-1}$ $cm^{-1}$ in PME buffer). Tubulin used in these experiments was detyrosinated using CPA and then retyrosinated with tyrosine (control) or 3-formyltyrosine using TTL prior to use as described above. Each tubulin sample was incubated with coumarin hydrazine in at least 1:10 molar ratio (tubulin:coumarin hydrazine) at RT for 120 min. Unreacted fluorophore was removed by rapid gel filtration. Labeled tubulin was visualized with a hand-held UV lamp after SDS-PAGE. An additional control experiment was performed in which TTL was excluded from the procedure. The maximum fluorescence intensity of these samples was approximately the same as the tyrosine control (FIG. 3, panel B, solid curve).

A number of other hydrazide fluorophores are available. See probes.invitrogen.com/servlets/pricelist?id=15399 (Life Technologies)
A10439 Alexa Fluor® 350 hydrazide, sodium salt
A10436 Alexa Fluor® 488 hydrazide, sodium salt
A20501 MP Alexa Fluor® 555 hydrazide, tris(triethylammonium) salt
A10437 Alexa Fluor® 568 hydrazide, sodium salt
A10438 Alexa Fluor® 594 hydrazide, sodium salt A30634 Alexa Fluor® 633 hydrazide, bis(triethylammonium) salt
A20502 Alexa Fluor® 647 hydrazide, tris(triethylammonium) salt
A10441 Alexa Fluor® 568 hydrazide, sodium salt (for microinjection) 10 mM in 200 mM KClA10442 Alexa Fluor® 594 hydrazide, sodium salt (for microinjection) 10 mM in 200 mM KCl
B1603 biocytin hydrazide
B2600 biotin-XX hydrazide (6-((6-((biotinoyl)amino) hexanoyl)amino) hexanoic acid, hydrazide)
C356 5-(((2-(carbohydrazino)methyl)thio) acetyl)aminofluorescein
C3239 Cascade Blue® hydrazide, trilithium salt
C3221 Cascade Blue® hydrazide, tripotassium salt
C687 Cascade Blue® hydrazide, trisodium salt
D355 7-diethylaminocoumarin-3-carboxylic acid, hydrazide (DCCH)
D2371 4,4-difluoro-5,7-dimethyl-4-bora-3a,4a-diaza-s-indacene-3-propionic acid, hydrazide (BODIPY® FL hydrazide)
D100 5-dimethylaminonaphthalene-1-sulfonyl hydrazine (dansyl hydrazine)
D20653 DSB-X™ biotin hydrazide
F121 fluorescein-5-thiosemicarbazide
L682 lucifer yellow CH, ammonium salt
L453 lucifer yellow CH, lithium salt
L12926 lucifer yellow CH, lithium salt (for microinjection) 100 mM in water
L1177 lucifer yellow CH, potassium salt
L8455 luminol (3-aminophthalhydrazide)
M20490 N-methyl-4-hydrazino-7-nitrobenzofurazan (NBD methylhydrazine)
P101 1-pyrenebutanoic acid, hydrazide
T6256 Texas Red® hydrazide *>90% single isomer*
  Some examples are:
  A10439 Alexa Fluor® 350 hydrazide, sodium salt

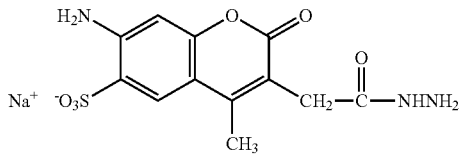

A10436 Alexa Fluor® 488 hydrazide, sodium salt

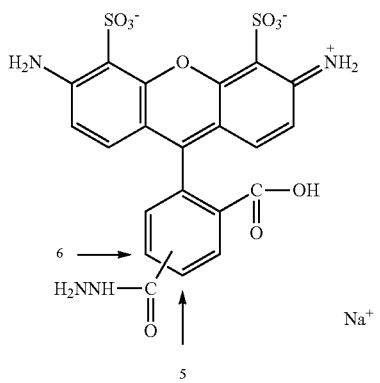

A20501MP Alexa Fluor® 555 hydrazide, tris(triethylammonium) salt

A10437 Alexa Fluor® 568 hydrazide, sodium salt

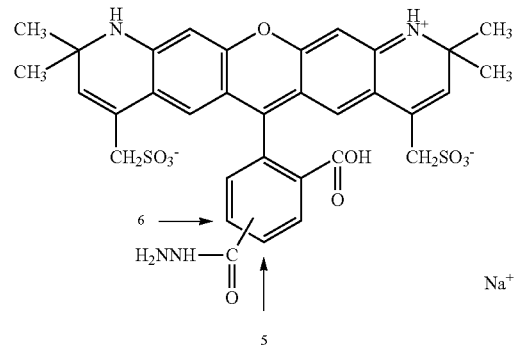

A10438 Alexa Fluor® 594 hydrazide, sodium salt

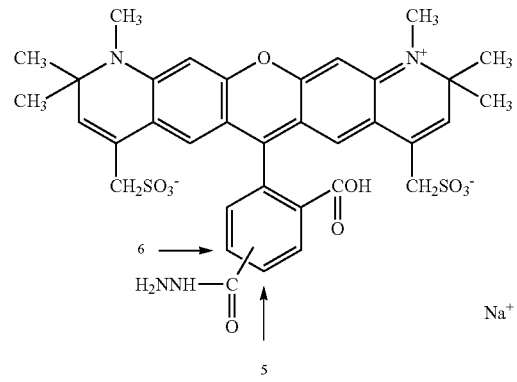

A30634 Alexa Fluor® 633 hydrazide, bis(triethylammonium) salt

A20502 Alexa Fluor® 647 hydrazide, tris(triethylammonium) salt

A10441 Alexa Fluor® 568 hydrazide, sodium salt (for microinjection) 10 mM in 200 mM KCl 125 μL

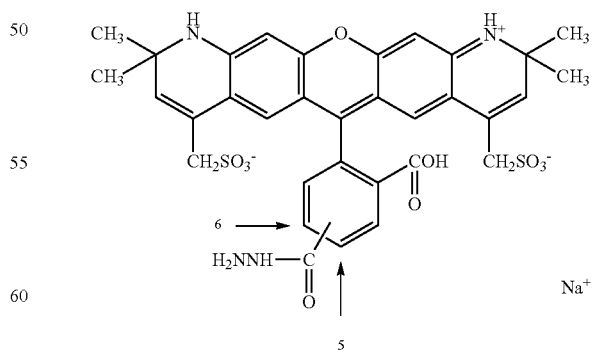

A10442 Alexa Fluor® 594 hydrazide, sodium salt (for microinjection) 10 mM in 200 mM KCl 125 μL

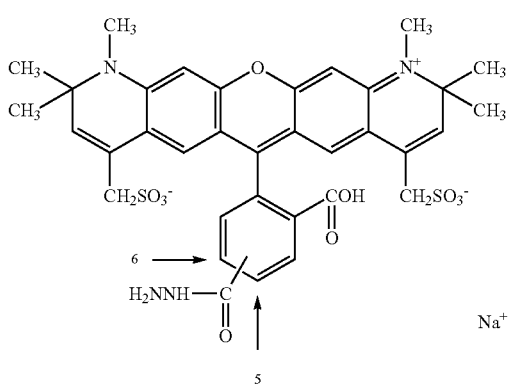

Aldehydes react with amines to form Schiff bases. Notable aldehyde-containing reagents described in Coumarins, Pyrenes and Other Ultraviolet Light-Excitable Fluorophores—Section 1.7 include o-phthaldialdehyde (OPA) and naphthalenedicarboxaldehyde (NDA), as well as the 3-acylquinolinecarboxaldehyde (ATTO-TAG) reagents CBQCA and FQ devised by Novotny and collaborators (Introduction to Amine Modification in catalog).

ATTO-TAG™ FQ Derivatization Reagent (FQ; 3-(2-Furoyl)quinoline-2-Carboxaldehyde)

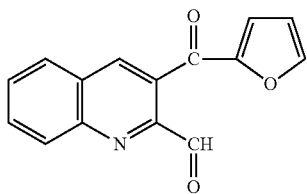 [SMILES: O=Cc1nc2ccccc2cc1C(=O)c1ccco1]

ATTO-TAG™ CBQCA Derivatization Reagent (CBQCA; 3-(4-Carboxybenzoyl)quinoline-2-Carboxaldehyde)

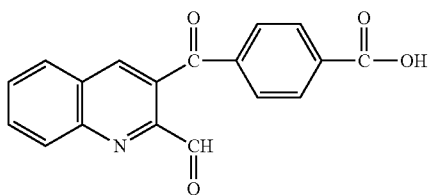 [SMILES: O=Cc1nc2ccccc2cc1C(=O)c1ccc(C(=O)O)cc1]

ATTO-TAG™ FQ Amine-Derivatization Kit

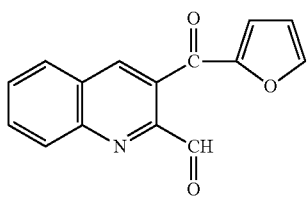 [SMILES: O=Cc1nc2ccccc2cc1C(=O)c1ccco1]

ATTO-TAG™ CBQCA Amine-Derivatization Kit

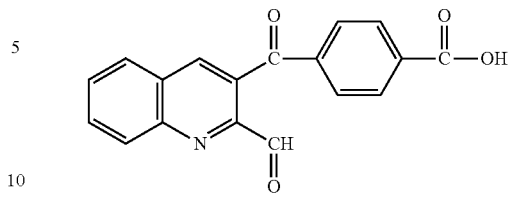

Fluorescent Labeling of Tubulin in Cells. Chinese hamster ovary (CHO) cells were grown in Ham's F-10 (tyrosine-depleted) medium in six-well plates. Semiconfluent cells were treated with 50 µM tyrosine or 3-formyltyrosine in medium and incubated at 37° C. overnight. The medium was discarded, and the cells were treated with 100 µM of coumarin hydrazine in fresh medium and incubated at 37° C. for 2 h. The medium was removed, and the cells were washed once with PBS. Lysis buffer (0.2 mL per well for a six-well plate) was added to each well and swirled to cover the whole area. The cells were scraped with a cell scraper and collected to one side of the well. The lysate was removed with a pipet to a microcentrifuge tube, and 1 µL mL$^{-1}$ of protease inhibitor cocktail was added. After shearing the extract using a 26.5 gauge needle, the samples were vortexed and then boiled for ~1 min. The extracts were separated using SDS-PAGE. Separate gels were stained for protein and visualized using a hand-held UV lamp or were analyzed by Western blot using a polyclonal anti-α-tubulin antibody.

Figure 10:
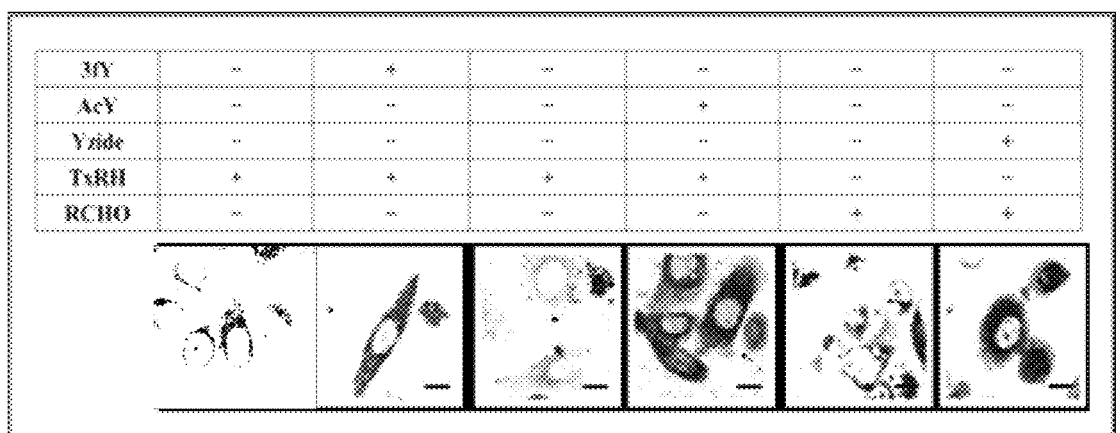
FIG. 10 shows labeling of microtubules in live cells. PC3 cells were grown in medium supplemented with or without unnatural amino acid. After removal of excess ligand, cells were briefly incubated with a suitably derivatized fluorophore. Excess fluorophore was washed off and a fluorescent photomicrograph was obtained, shown as brighfield.

As shown in FIG. 10, the process for labeling microtubules in live cells proceeds as follows. PC3 cells were grown in medium supplemented with unnatural amino acid for 10-24 h. After removal of excess ligand, cells were briefly incubated with a suitably derivatized fluorophore. Excess fluorophore was washed off and photomicrograph was obtained. Microtubule bundles in live cells were labeled as follows. PC3 cells were grown in medium supplemented with unnatural amino acid for 10-24 h. Cells were then treated with Taxol for 4-24 h. After removal of excess ligand, cells were briefly incubated with a suitably derivatized fluorophore. Excess fluorophore was washed off and photomicrograph was obtained.

The present technology therefore provides the ability to label structures within living cells based on the ability of endogenous post translational modification enzymes to add derivatized bioorthogonal tags, and reacting the ligated derivatized tag with a label, such as a fluorphore. Because post translation modification enzymes tend to be substrate specific, and a particular target may have multiple modifications, fluorescent energy resonance transfer technology may be used to detect dual-labeled molecules with short distances between the labels. A preferred embodiment employs derivatized tyrosine or tyrosine analogs and the post translational modification enzyme tubulin tyrosine ligase, but other enzyme-substrate systems may be used, such as glycosylation enzymes, glutamyl transferases, glycine transferases, etc. The preferred derivitization permits rapid, specific and nearly quantitative labeling, e.g., with the fluorophore, and therefore minimizes the need for long labeling reactions extensive washing after the labeling reaction. The preferred tags and labels have low cellular toxicity, and therefore do not interfere with cellular processes being monitored.

FIG. 1 shows that 3-Formyltyrosine is incorporated into alpha-tubulin. Carboxypeptidase A (CPA) treated tubulin was incubated with tubulin tyrosine ligase in the presence of either L-tyrosine or 3-formyltyrosine and then subjected to SDS-PAGE. Top: Western blot with tyrosinated α-tubulin antibody (Sigma-Aldrich TUB-1A2). Bottom: Coomassie stain. Lane 1: Tubulin. Lane 2: Tubulin treated with CPA. Lane 3: CPA-treated tubulin retyrosinated with tyrosine. Lane 4: CPA-treated tubulin retyrosinated with 3-formyltyrosine. The mass of protein loaded each well was 0.66 µg for the Western blot and 10 µg for the protein stain.

Figure 2:
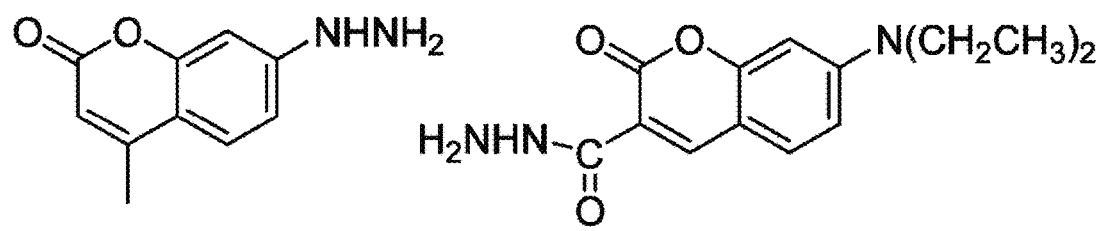
FIG. 2 shows structures of coumarin hydrazine and coumarin hydrazide.

FIG. 2 shows the structures of coumarin hydrazine and coumarin hydrazide.

FIG. 3A shows kinetics of hydrazone formation between coumarin hydrazine and 3-formyltyrosine. Coumarin hydrazine (25 µM) was mixed with 3-formyltyrosine (250 UM) in PME buffer (pH 6.9) at 25° C. The absorption difference spectrum was collected at 5 min intervals and the change in absorption at 384 nm was plotted. Solid line: Fit of data to a single exponential.

FIG. 3B shows an emission spectrum of fluorescently labeled tubulin. CPA-treated tubulin was retyrosinated with L-tyrosine (solid curve) or 3-formyltyrosine (dotdash curve) followed by treatment of coumarin hydrazine as described under Methods. Each sample contained 2 µM tubulin. The excitation wavelength was 392 nm.

Figure 4:
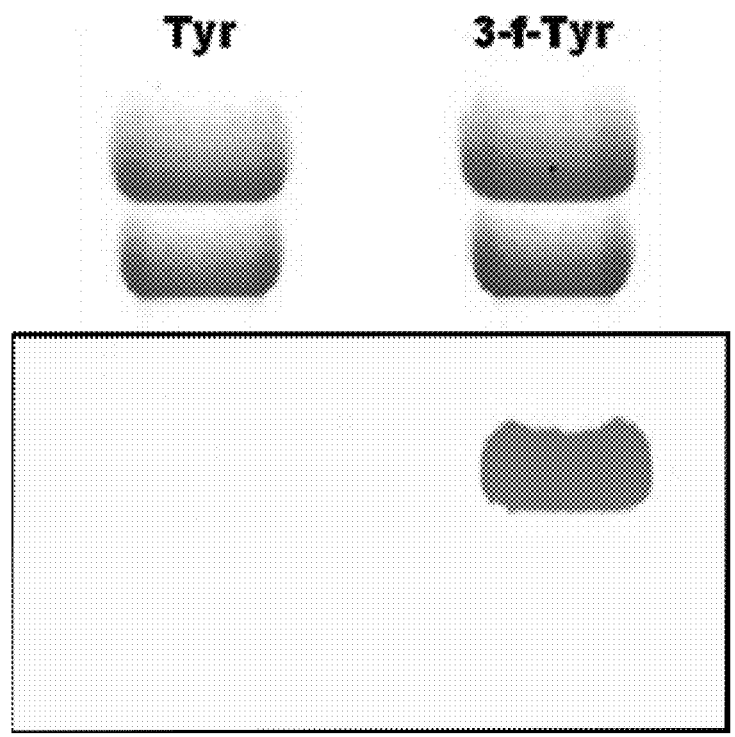
FIG. 4 shows coumarin hydrazine covalently binds to 3-formyltyrosinated α-tubulin. CPA-treated tubulin, tyrosinated using TTL and 3-formyltyrosine (left) or L-tyrosine (right), at a final concentration of 30 µM was treated with 100 µM of coumarin hydrazine in PME buffer prior to SDSPAGE. The upper band in the gel is α-tubulin and the lower band is α-tubulin. Top: Coomassie stain. Bottom: Fluorescence under long wavelength UV lamp (shown as brightfield).

FIG. 4 shows that coumarin hydrazine covalently binds to 3-formyltyrosinated α-tubulin. CPA-treated tubulin, tyrosinated using TTL and 3-formyltyrosine (left) or L-tyrosine (right), at a final concentration of 30 was treated with 100 of coumarin hydrazine in PME buffer prior to SDSPAGE. The upper band in the gel is α-tubulin and the lower band is p-tubulin. Top: Coomassie stain. Bottom: Fluorescence under long wavelength UV lamp.

Figure 5:
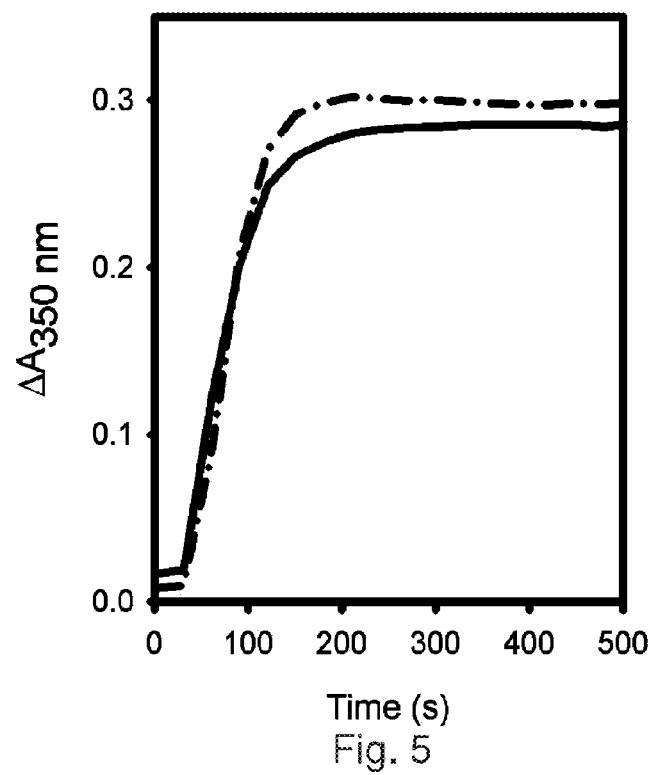
FIG. 5 shows fluorescently labeled tubulin retains assembly activity. CPA-treated tubulin (5 µM), retyrosinated with either L-tyrosine (solid curve) or 3-formyltyrosine (dot-dash curve) and treated with coumarin hydrazine, was polymerized with paclitaxel (5 µM) in PMEG buffer at 37° C.

FIG. 5 shows that fluorescently labeled tubulin retains assembly activity. CPA-treated tubulin (5 µM), retyrosinated with either L-tyrosine (solid curve) or 3-formyltyrosine (dot-dash curve) and treated with coumarin hydrazine, was polymerized with paclitaxel (5 µl) in PMEG buffer at 37° C.

FIGS. 6A-6D show that hydrazone formation occurs in live cells and is accompanied by an increase in probe fluorescence. PC3 cells were grown to 50% confluence in Ham's F-10 medium. The cells were incubated for 24 h with fresh medium supplemented with 50 µM L-tyrosine (FIGS. 6A and 6B) or 50 µM 3-formyltyrosine (FIGS. 6C and 6D). After the cells were washed with fresh medium, medium containing 20 coumarin hydrazine was added, and the cells were observed under laser scanning confocal microscope. FIGS. 6A and 6C: Fluorescence images using violet laser diode excitation (405 nm) and emission bandpass of 420-480 nm. FIGS. 6B and 6D: Differential interference contrast images.

Figures 7A, 7B, 7C:
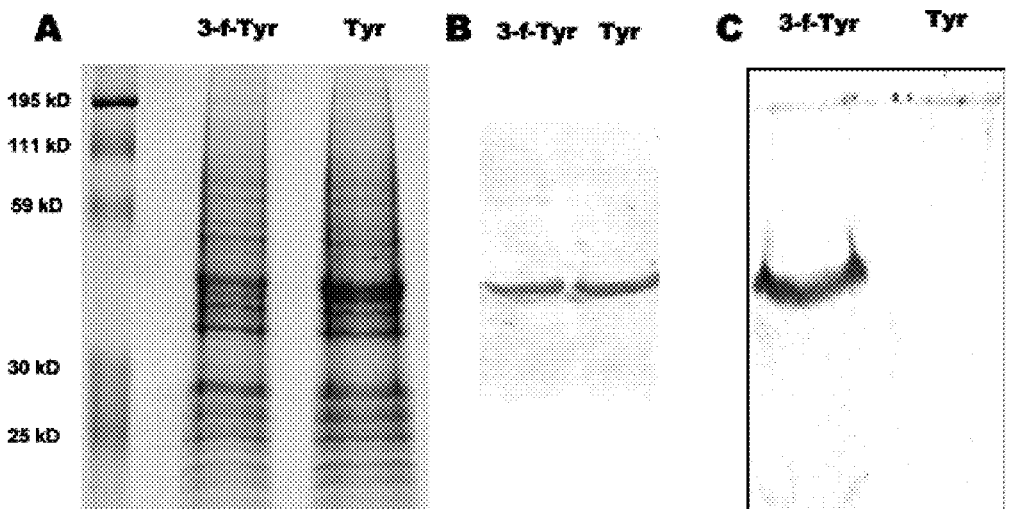
FIGS. 7A-7C show α-Tubulin is the only fluorescently labeled protein observed in cells incubated with 3-formyltyrosine followed by coumarin hydrazine treatment. CHO cells were incubated for 24 h in Ham's F-10 medium containing 50 µM L-tyrosine or 50 µM 3-formyltyrosine. The cells were washed and then treated with coumarin hydrazine (100 µM) for 2 h. Cells were harvested and lysed, and the lysate was separated using SDS-PAGE.

FIGS. 7A-7C show that α-Tubulin is the only fluorescently labeled protein observed in cells incubated with 3-formyltyrosine followed by coumarin hydrazine treatment. CHO cells were incubated for 24 h in Ham's F-10 medium containing 50 L-tyrosine or 50 µM 3-formyltyrosine. The cells were washed and then treated with coumarin hydrazine (100 µM) for 2 h. Cells were harvested and lysed, and the lysate was separated using SDS-PAGE. FIG. 7A shows Coumassie stain. FIG. 7B shows a Western blot of lystate using a polyclonal antibody to α-tubulin. FIG. 7C shows a Gel of the lysate visualized under long wavelength UV light.

Figure 8:
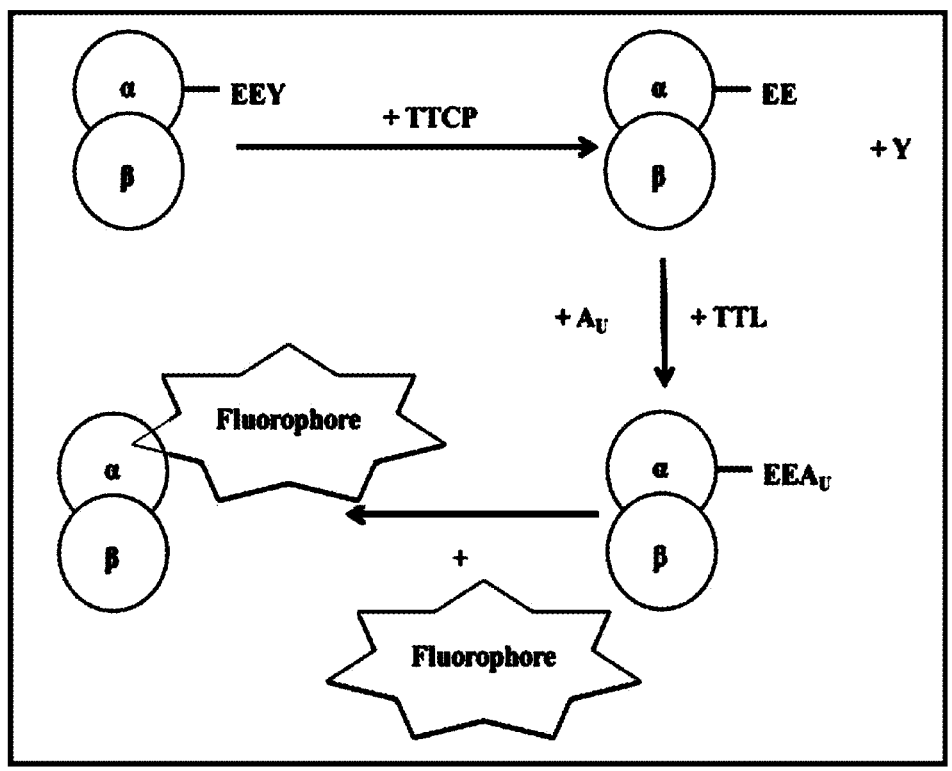
FIG. 8 shows Labeling of Tubulin.

FIG. 8 shows a schematic diagram of Tubulin labeling. Y=Tyrosine; Glutamic acid; TTCP=Tubulin tyrosine carboxypeptidase; TTL=Tubulin tyrosine ligase; $A_U$=Unnatural amino acid=3fY (3-formyltyrosine)/AcY(3-acetyltyrosine)/ Yzide (tyrosine hydrazide); Fluorophore=TxRH (Texas Red hydrazide)/Rosamine aldehyde (RCHO)

Figure 9:
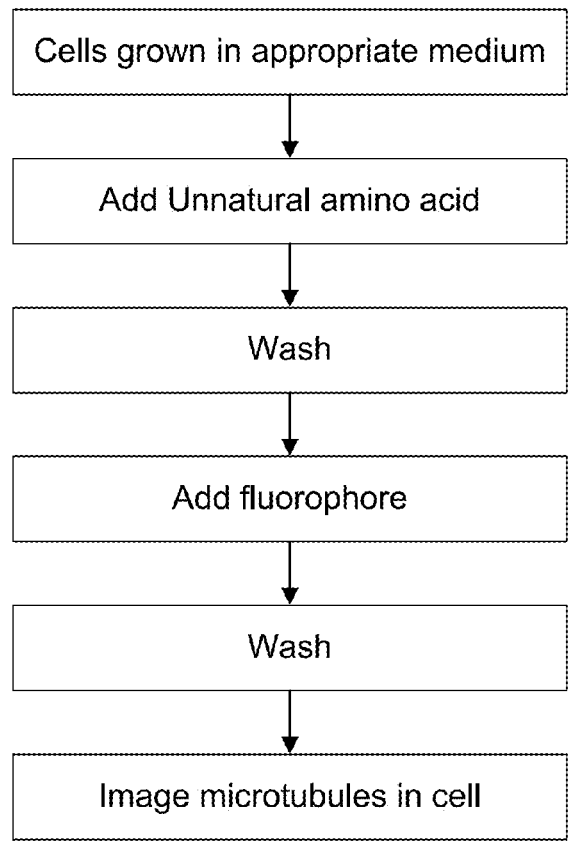
FIG. 9 shows labeling in cells. PC3 cells were grown in medium supplemented with or without unnatural amino acid. After removal of excess ligand, cells were briefly incubated with a suitably derivatized fluorophore. Excess fluorophore was washed off and a fluorescent photomicrograph was obtained.

FIG. 9 shows a schematic flowchart for labeling in cells.

FIG. 10 shows a table of results for labeling microtubules in live cells. PC3 cells were grown in medium supplemented with or without unnatural amino acid for 15-24 h. After removal of excess ligand, cells were briefly incubated with a suitably derivatized fluorophore. Excess fluorophore was washed off and photomicrograph was obtained.

Figure 11:
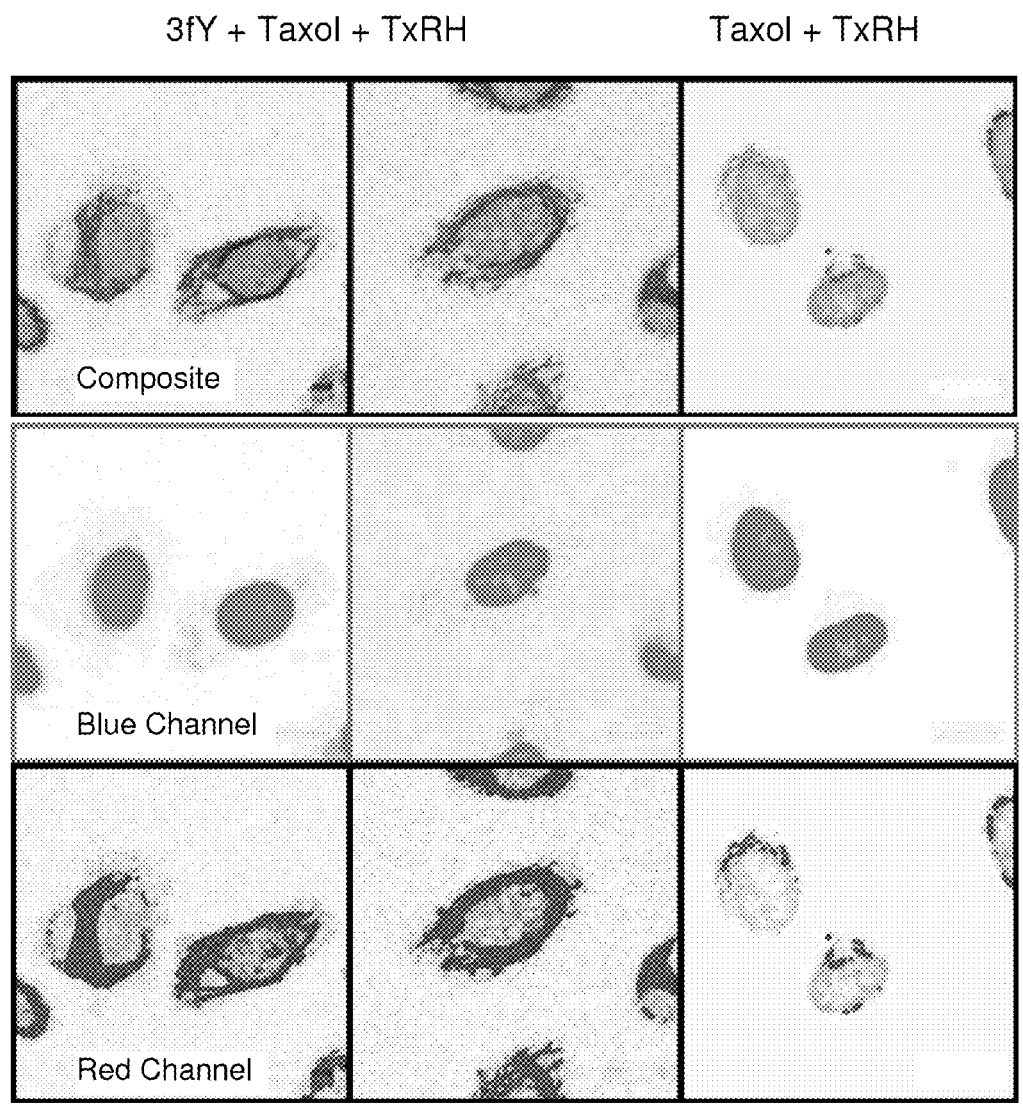
FIG. 11 shows labeling of microtubules in live cells. PC3 cells were grown in medium supplemented with or without 3-formyl tyrosine (3fY). Cells were then treated with taxol. After removal of excess ligand, cells were incubated with NucBlue (Life Technologies). Cells were then briefly incubated with TxRH. Excess fluorophore was washed off and photomicrograph was obtained.

FIG. 11 shows fluorescent micrographs showing labeling of microtubules in live cells. PC3 cells were grown in medium supplemented with 3fY. Cells were then treated with Taxol. After removal of excess ligand, cells were incubated with NucBlue (Life Technologies). Cells were then briefly incubated with TxRH. Excess fluorophore was washed off and photomicrograph was obtained.

Figure 12A:
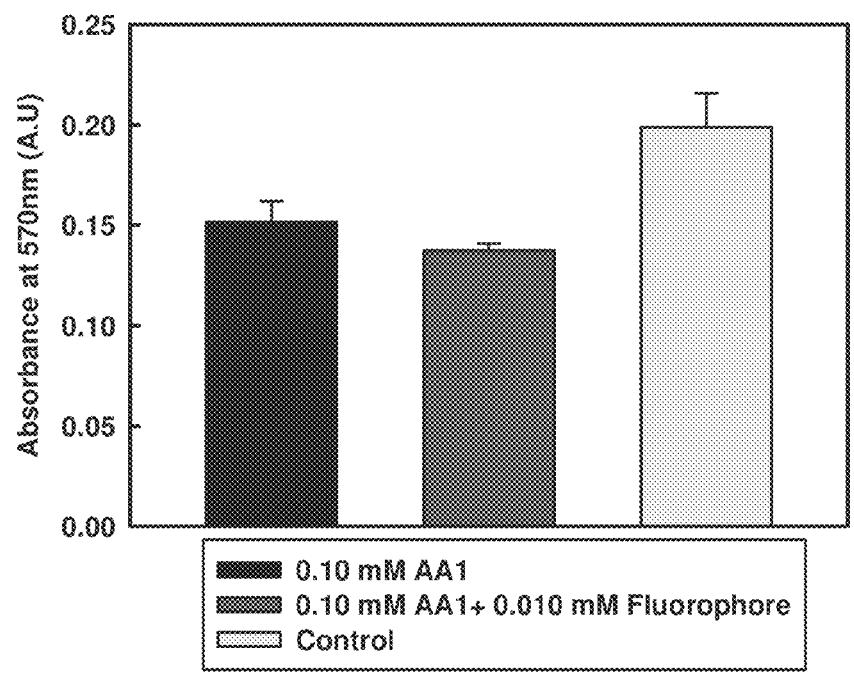
FIGS. 12A-12C shows graphs of cytotoxicity of amino acid and fluorophore on live cells. PC3 cells were grown in medium supplemented with unnatural amino acid or vehicle for 24 h. Cells were then treated with fluorophore or vehicle for 24 h, following which an SRB assay was performed to assess the cytotoxicity of the molecules.
Figure 12B:
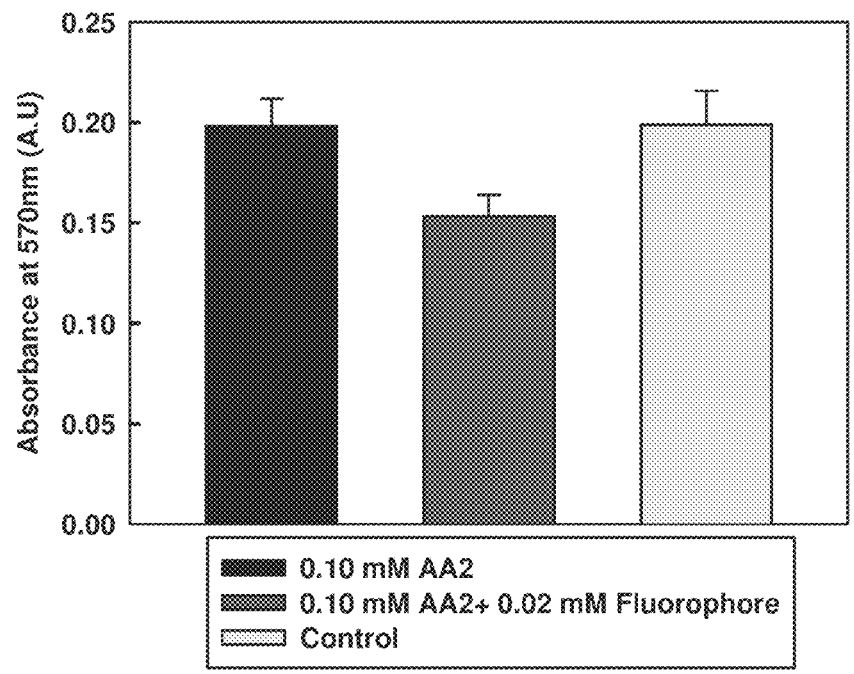
Figure 12C:
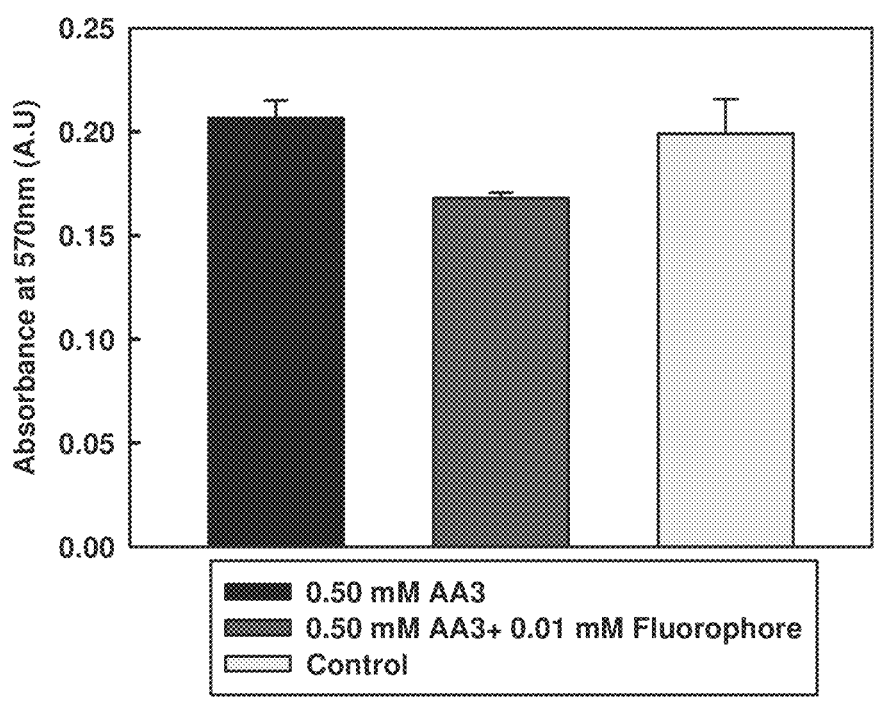

FIGS. 12A-12C show graphs of cytotoxicity of amino acid and fluorophore on live cells. The labeling technique is not detrimental to PC3 cell survival. PC3 cells were grown in medium supplemented with unnatural amino acid or vehicle (2% v/v, 10 mM phosphate buffer, pH 7) for 24 h. Cells were then treated with fluorophore or vehicle (1% v/v DMSO) for 24 h. Following which SRB assay was performed to assess the cytotoxicity of the molecules.

Figure 13:
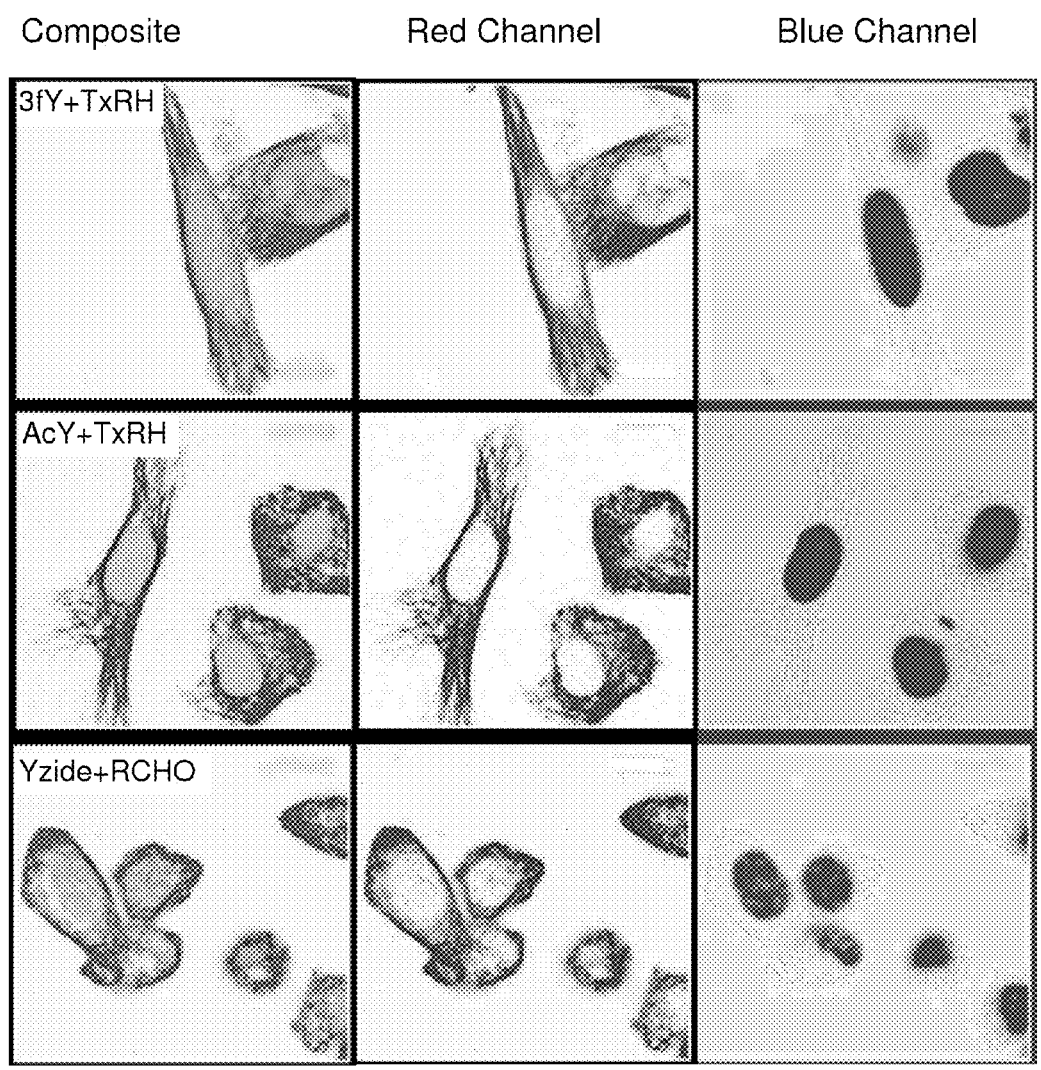
FIG. 13 shows the effect of amino acid and fluorophore on live cells on cell morphology and microtubule network. PC3 cells were grown in F12K medium supplemented with unnatural amino acid for 24 h. Cells were washed and then treated with fluorophores for 24 h before fixing with methanol. Cells were then processed for immunofluorescence using tubulin antibody (red) and DAPI (blue).

FIG. 13 shows the effect of amino acid and fluorophore on live cells, on cell morphology, and microtubule network. PC3 cells were grown in F12K medium supplemented with unnatural amino acid for 24 h. Cells were washed and treated with a fluorophore for 24 h before fixing with methanol. Cells were then processed for immunofluorescence using tubulin antibody (red) and DAPI (blue). The top micrograph shows 3fY and TxRH, the middle micrograph shows AcY and TxRH and the bottom micrograph shows Yzide and RCHO.

Figure 14:
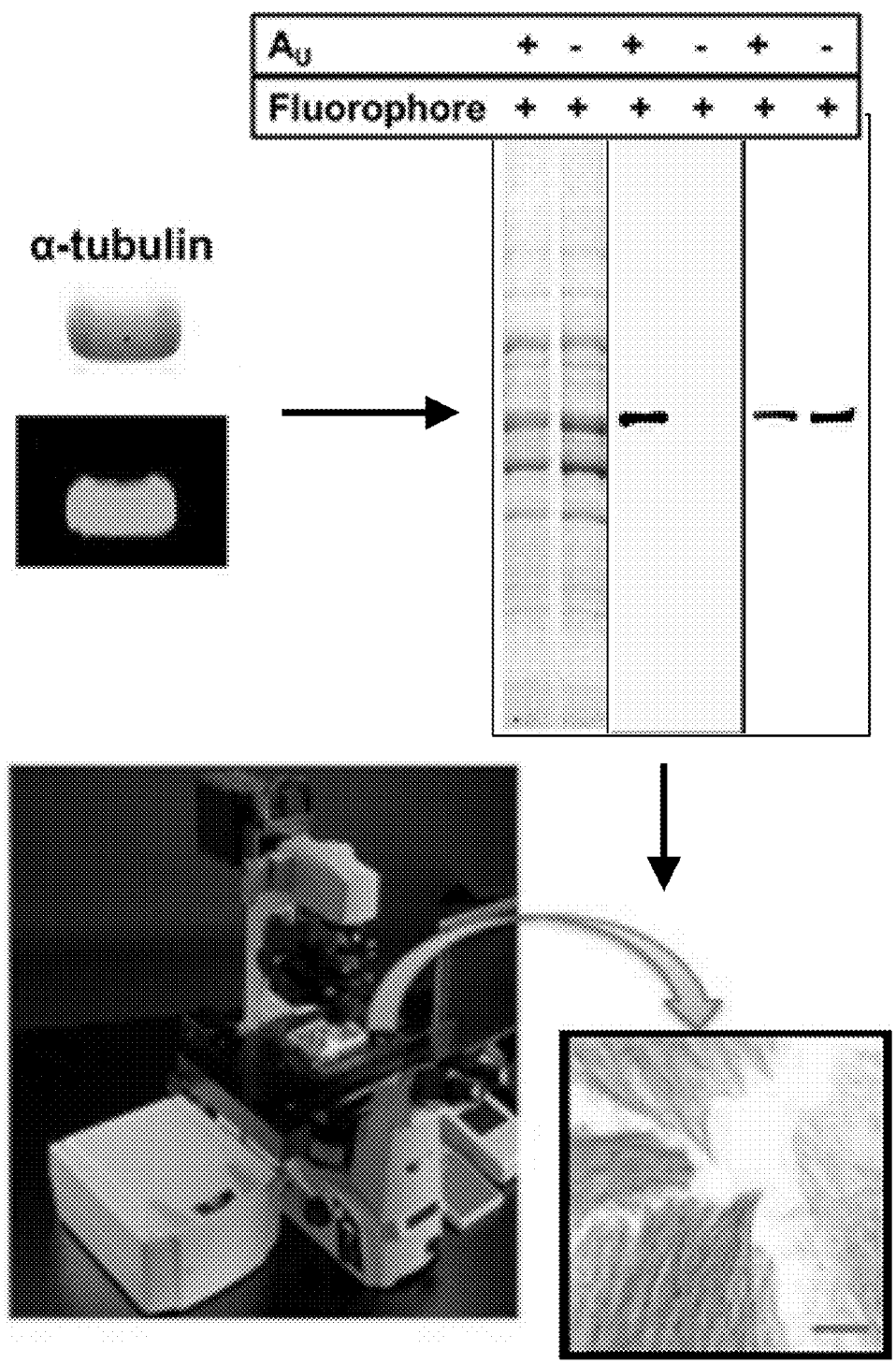
FIG. 14 shows a schematic representation of the method for use of un-natural bio-orthogonal amino acid and fluorphore labeling in live cells.

FIG. 14 shows the use of un-natural bio-orthoginal amino acid and fluorphore labelling in live cells.

Figure 15A:
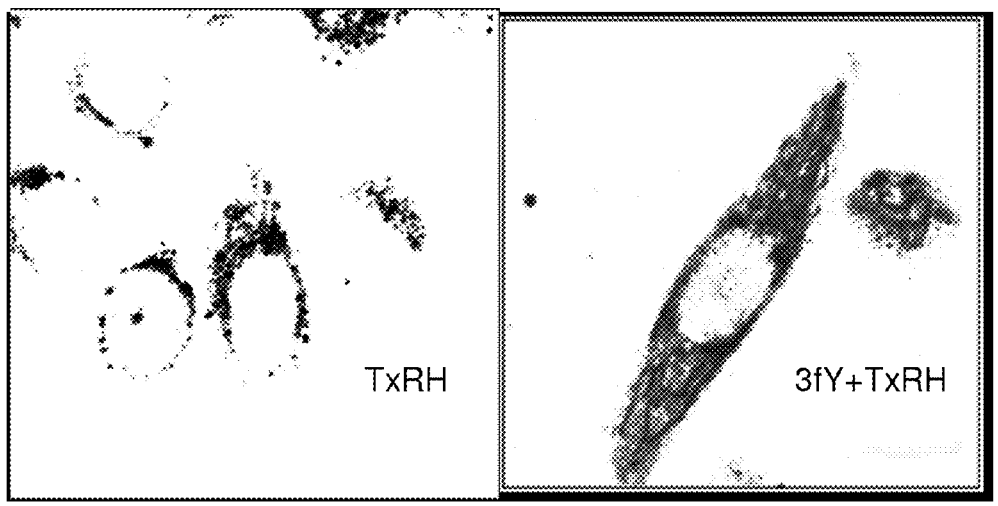
FIGS. 15A-15C show microtubules in live cells, using 3-formyltyrosine, 3-acetyltyrosine or tyrosine hydrazide and suitably derivatized fluorophore as brightfield fluorescent micrograph images of the cells.
Figure 15B:
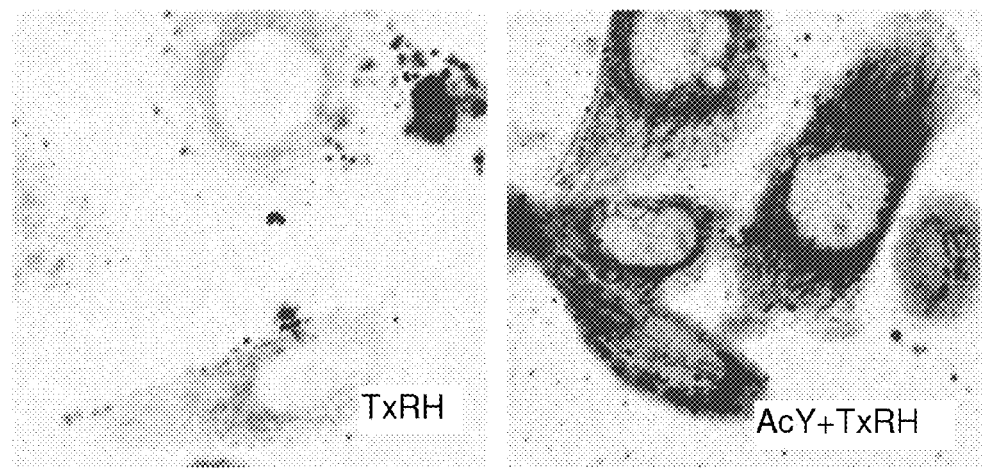
Figure 15C:
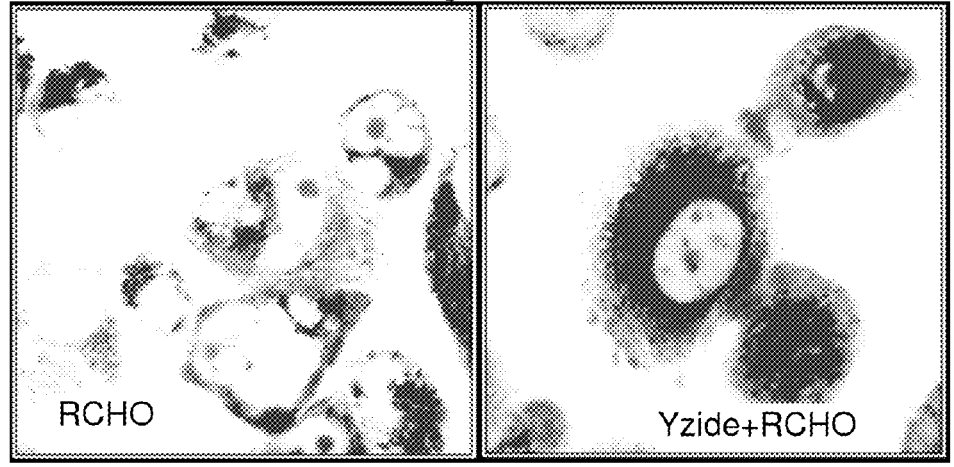

FIGS. 15A-15C show microtubules in live cells. FIG. 15A shows TxRH and 3fY+TxRH. FIG. 15B shows TxRH and AcY+TxRH. FIG. 15C shows RCHO and Yzide+ RCHO. Reduced size versions of these appear in FIG. 10.

Figure 16:
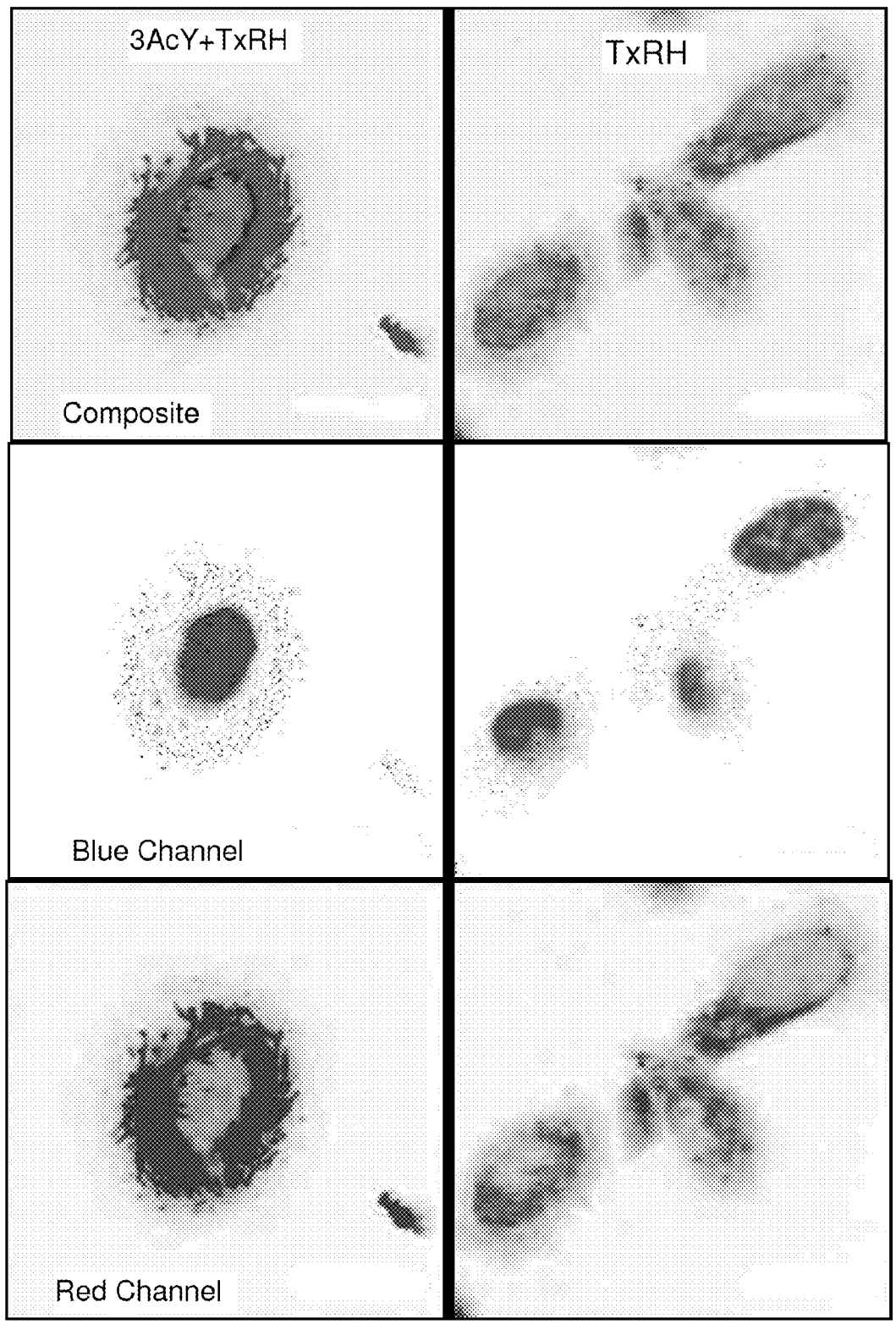
FIG. 16 shows taxol-induced microtubule bundles in live cells, showing composite, red channel and blue channel images for fluorphore alone or in combination with 3-acetyl tyrosine (3-AcY), shown as brightfield fluorescent micrograph images of the cells.

FIG. 16 shows labeling of microtubule bundles in live cells. The left and middle panes show 3-acetyl tyrosine+ Taxol+fluorophore, and the right pane shows taxol+fluorophore.

REFERENCES (EACH OF WHICH IS EXPRESSLY INCORPORATED HEREIN BY REFERENCE)

1. Avila, J. (1990) Microtubule Proteins, CRC Press, Boca Raton, Fla.
2. Jordan, M. A., and Wilson, L. (1998) Microtubules and actin filaments: dynamic targets for cancer chemotherapy, Curr. Opin. Cell Biol. 10, 123-130.
3. Hammond, J. W., Cai, D. W., and Verhey, K. J. (2008) Tubulin modifications and their cellular functions, Curr. Opin. Cell Biol. 20, 71-76.
4. Westermann, S., and Weber, K. (2003) Post-translational modifications regulate microtubule function, Nat. Rev. Cell Mol. Biol. 4, 938-947.
5. Nogales, E., Wolf, S. G., and Downing, K. H. (1998) Structure of the alpha beta tubulin dimer by electron crystallography, Nature 391, 199-203.
6. Gigant, B., Curmi, P. A., Martin-Barbey, C., Charbaut, E., Lachkar, S., Lebeau, L., Siavoshian, S., Sobel, A., and Knossow, M. (2000) The 4 Å X-ray structure of a tubulin: stathmin-like domain complex, Cell 102, 809-816.

7. Priel, A., Tuszynski, J. A., and Woolf, N. J. (2005) Transitions in microtubule C-termini conformations as a possible dendritic signaling phenomenon, Eur. Biophys. J. 35, 40-52.
8. Erck, C., Frank, R., and Wehland, J. (2000) Tubulin-tyrosine ligase, a long-lasting enigma, Neurochem. Res. 25, 5-10.
9. Wehland, J., Schroder, H. C., and Weber, K. (1986) Isolation and purification of tubulin tyrosine ligase, Methods Enzymol. 134, 170-179.
10. Ersfeld, K., Wehland, J., Plessmann, U., Dodemont, H., Gerke, V., and Weber, K. (1993) Characterization of the tubulin tyrosine ligase, J. Cell Biol. 120, 725-732.
11. Erck, C., Peris, L., Andrieux, A., Meissirel, C., Gruber, A. D., Vernet, M., Schweitzer, A., Saoudi, Y., Pointu, H., Bosc, C., Salin, P. A., Job, D., and Wehland, J. (2005) A vital role of tubulin-tyrosine-ligase for neuronal organization, Proc. Natl. Acad. Sci. U.S.A. 102, 7853-7858.
12. Skoufias, D. A., and Wilson, L. (1998) Assembly and colchicine binding characteristics of tubulin with maximally tyrosinated and detyrosinated alpha-tubulins, Arch. Biochem. Biophys. 351, 115-122.
13. Webster, D. R., Wehland, J., Weber, K., and Borisy, G. G. (1990) Detyrosination of alpha-tubulin does not stabilize microtubules in vivo, J. Cell Biol. 111, 113-122.
14. Mialhe, A., Lafanechere, L., Treilleux, I., Peloux, N., Dumontet, C., Bremond, A., Panh, M. H., Payan, R., Wehland, J., Margolis, R. L., and Job, D. (2001) Tubulin detyrosination is a frequent occurrence in breast cancers of poor prognosis, Cancer Res. 61, 5024-5027.
15. Kato, C., Miyazaki, K., Nakagawa, A., Ohira, M., Nakamura, Y., Ozaki, T., Imai, T., and Nakagawara, A. (2004) Low expression of human tubulin tyrosine ligase and suppressed tubulin tyrosination/detyrosination cycle are associated with impaired neuronal differentiation in neuroblastomas with poor prognosis, Int. J. Cancer 112, 365-375.
16. Soucek, K., Kamaid, A., Phung, A. D., Kubala, L., Bulinski, J. C., Harper, R. W., and Eiserich, J. P. (2006) Normal and prostate cancer cells display distinct molecular profiles of alpha-tubulin posttranslational modifications, Prostate 66, 954-965.
17. Shah, C., Xu, C. Z. Q., Vickers, J., and Williams, R. (2001) Properties of microtubules assembled from mammalian tubulin synthesized in *Escherichia coli*, Biochemistry 40, 4844-4852.
18. Andresen, M., Schmitz-Salue, R., and Jakobs, S. (2004) Short tetracysteine tags to beta-tubulin demonstrate the significance of small labels for live cell imaging, Mol. Biol. Cell 15, 5616-5622.
19. Prasad, A. R. S., Luduena, R. F., and Horowitz, P. M. (1986) Bis(8-anilinonaphthalene-1-sulfonate) as a probe for tubulin decay, Biochemistry 25, 739-742.
20. Lee, H. S., Guo, J. T., Lemke, E. A., Dimla, R. D., and Schultz, P. G. (2009) Genetic Incorporation of a small, environmentally sensitive, fluorescent probe into proteins in *Saccharomyces cerevisiae*, J. Am. Chem. Soc. 131, 12921-12923.
21. Katritzky, A. R., and Narindoshvili, T. (2009) Fluorescent amino acids: advances in protein-extrinsic fluorophores, Org. Biomol. Chem. 7, 627-634.
22. Arce, C. A., Rodriguez, J. A., Barra, H. S., and Caputo, R. (1975) Incorporation of L-tyrosine, L-phenylalanine and L-3,4-dihydroxyphenylalanine as single units into rat brain tubulin, Eur. J. Biochem. 59, 145-149.
23. Monasterio, O., Nova, E., Lopezbrauet, A., and Lagos, R. (1995) Tubulin-tyrosine ligase catalyzes covalent binding of 3-fluorotyrosine to tubulin—kinetic and [F-19] NMR Studies, FEBS Lett. 374, 165-168.
24. Kalisz, H. M., Erck, C., Plessmann, U., and Wehland, J. (2000) Incorporation of nitrotyrosine into alpha-tubulin by recombinant mammalian tubulin-tyrosine ligase, Biochem. Biophys. Acta 1481, 131-138.
25. Coudijzer, K., and Joniau, M. (1990) 3-Azido-L-tyrosine as a photoinhibitor of tubulin-tyrosine ligase. Role of thiol-groups, FEBS Lett. 268, 95-98.
26. Bisig, C. G., Purro, S. A., Contin, M. A., Barra, H. S., and Arce, C. A. (2002) Incorporation of 3-nitrotyrosine into the C-terminus of $\alpha$-tubulin is reversible and not detrimental to dividing cells, Eur. J. Biochem. 269, 5037-5045.
27. Mihm, M. J., Schanbacher, B. L., Wallace, B. L., Wallace, L. J., Uretsky, N. J., and Bauer, J. A. (2001) Free 3-nitrotyrosine causes striatal neurodegeneration in vivo, J. Neurosci. 21, (RC149), 1-5.
28. Eiserich, J. P., Estevez, A. G., Bamberg, T. V., Ye, Y. Z., Chumley, P. H., Beckman, J. S., and Freeman, B. A. (1999) Microtubule dysfunction by posttranslational nitrotyrosination of alpha-tubulin: A nitric oxide-dependent mechanism of cellular injury, Proc. Natl. Acad. Sci. U.S.A. 96, 6365-6370.
29. Moses, J. E., and Moorhouse, A. D. (2007) The growing applications of click chemistry, Chem. Soc. Rev. 36, 1249-1262.
30. Jean-Francois, L. (2008) Copper-free azide-alkyne cycloadditions: new insights and perspectives, Angew. Chem. 47, 2182-2184.
31. Liliom, K., Wagner, G., Pacz, A., Cascante, M., Kovacs, J., and Ovadi, J. (2000) Organization-dependent effects of toxic bivalent ions—microtubule assembly and glycolysis, Eur. J. Biochem. 267, 4731-4739.
32. Rudiger, M., and Weber, K. (1993) Characterization of the posttranslational modifications in tubulin from the marginal band of avian erythrocytes, Eur. J. Biochem. 218, 107-116.
33. Jencks, W. P. (1964) Mechanism and Catalysis of Simple Carbonyl Group Reactions, in Progress in Physical Organic Chemistry (Cohen, S. G., Streitwieser, A., Jr., and Taft, R. W., Eds.), Vol. 2, pp 63-128, John Wiley & Sons, Inc., New York.
34. Smith, P. A. S. (1983) Derivatives of Hydrazine and Other Hydronitrogens Having N—N Bonds, The Benjamin/Cummings Publishing Company, Reading, Mass.
35. Dirksen, A., and Dawson, P. E. (2008) Rapid oxime and hydrazone ligations with aromatic aldehydes for biomolecular labeling, Bioconjugate Chem. 19, 2543-2548.
36. Dilek, O., and Bane, S. L. (2008) Synthesis of boron dipyrromethene fluorescent probes for bioorthogonal labeling, Tetrahedron Lett. 49, 1413-1416.
37. Valeur, B. (2002) Molecular Fluorescence Principles and Applications, Wiley-VCH, Weinheim.
38. Vogel, M., Buldt, A., and Karst, U. (2000) Hydrazine reagents as derivatizing agents in environmental analysis—a critical review, Fresenius' J. Anal. Chem. 366, 781-791.
39. Sackett, D. L. (1995) Structure and Function in the Tubulin Dimer and the Role of the Acidic Carboxy Terminus, in Proteins: Structure, Function and Engineering (Biswas, B. B., and Roy, S., Eds.), pp 255-302, Plenum Press, New York.
40. Xie, J. M., and Schultz, P. G. (2006) Innovation: A chemical toolkit for proteins—an expanded genetic code, Nat. Rev. Cell Mol. Biol. 7, 775-782.

41. Liu, W. S., Brock, A., Chen, S., Chen, S. B., and Schultz, P. G. (2007) Genetic incorporation of unnatural amino acids into proteins in mammalian cells, Nat. Methods 4, 239-244.

42. Do Amaral, L., and Bastos, M. P. (1971) Kinetics and mechanism for benzaldehyde phenylhydrazone formation, J. Org. Chem. 36, 3412-3417.

43. Alves, K. B., Bastos, M. P., and Do Amaral, L. (1978) Mechanism and catalysis for o-hydroxyacetophenone phenylhydrazone formation, J. Org. Chem. 43, 4032-4038.

44. Williams, R. C., and Lee, J. C. (1982) Purification of tubulin from brain, Methods Enzymol. 85, 376-385.

45. A. Desai, T. J. Mitchison, Microtubule polymerization dynamics, Annual review of cell and developmental biology 13 (1997) 83-117.

46. H. V. Goodson, J. S. Dzurisin, P. Wadsworth, Methods for expressing and analyzing GFP-tubulin and GFP-microtubule-associated proteins, Cold Spring Harbor protocols 2010 (2010) pdb.top85-pdb.top85.

47. S. Okabe, N. Hirokawa, Microtubule Dynamics in Nerve-Cells—Analysis Using Microinjection of Biotinylated Tubulin into PC12 Cells, Journal of Cell Biology 107 (1988) 651-664.

48. I. Barasoain, J. Fernando Diaz, J. M. Andreu, Fluorescent Taxoid Probes for Microtubule Research, in: L. Wilson, J. J. Correia (Eds.), Microtubules, in Vitro 2010, pp. 353-372.

49. C. Janke, J. C. Bulinski, Post-translational regulation of the microtubule cytoskeleton: mechanisms and functions, Nature Reviews Molecular Cell Biology 12 (2011) 773-786.

What is claimed is:

1. A method for labeling microtubules in living cells, comprising incubating the living cells with tyrosine hydrazide for a sufficient time for the tyrosine hydrazide to be ligated to alpha tubulin by tubulin tyrosine ligase, and then adding a cell membrane permeable label comprising a rosamine aldehyde, wherein the hydrazide of the tyrosine hydrazide spontaneously reacts with the aldehyde or ketone of the label to form a covalent bond.

2. The method according to claim 1, wherein the membrane permeable label spontaneously reacts with the hydrazide functionality of the tyrosine hydrazide to form a covalent bond substantially without toxicity to the living cells.

3. The method according to claim 1, wherein the label comprises a fluorescent probe.

4. The method according to claim 1, further comprising acquiring a fluorescent image of the label showing the microtubules.

5. The method of claim 1, wherein the rosamine aldehyde comprises (1-(9-(4-formylphenyl)-6-(pyrrolidin-1-yl)-3H-xanthen-3-ylidene)pyrrolidine or its HCl salt: (1-(9-(4-formylphenyl)-6-(pyrrolidin-1-yl)-3H-xanthen-3-ylidene)pyrrolidinium chloride).

6. The method according to claim 1, wherein the rosamine aldehyde comprises a composition having formula I:

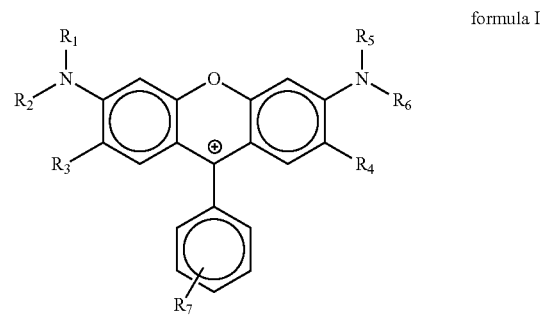

formula I wherein $R_7$ is an alkyl or aryl comprising an aromatic aldehyde moiety;

$R_3$ and $R_4$ are the same or different selected from the group consisting of hydrogen, substituted or unsubstituted alkyl, aryl, heteroalkyl, heteroaryl, haloalkyl, and haloaryl; and $R_1$ and $R_2$, and $R_5$ and $R_6$, are the same or different or $R_1$ and $R_2$, or $R_5$ and $R_6$ together form a ring having at least 5 members, selected from the group consisting of substituted or unsubstituted alkyl, aryl, heteroalkyl, heteroaryl, haloalkyl, and haloaryl, wherein the rosamine aldehyde is at least one of soluble in water or lipid membranes.

7. The method according to claim 6, wherein $R_1$ and $R_2$ are together pyrrolidine and $R_5$ and $R_6$ are together pyrrolidine.

8. The method according to claim 6, wherein $R_7$ is a 4-formylphenyl group, the rosamine aldehyde comprising (1-(9-(4-formylphenyl)-6-(pyrrolidin-1-yl)-3H-xanthen-3-ylidene)pyrrolidine or its HCl salt: (1-(9-(4-formylphenyl)-6-(pyrrolidin-1-yl)-3H-xanthen-3-ylidene)pyrrolidinium chloride).

9. The method according to claim 6, wherein $R_3$ and $R_4$ are hydrogen, $R_7$ is 4-formylphenyl, and $R_1$ and $R_2$ together and $R_5$ and $R_6$ together, are each:

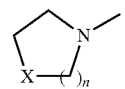

wherein X is $CH_2$, O or NR, n is 1 or 2, and R is hydrogen, substituted or unsubstituted alkyl, aryl, heteroalkyl, heteroaryl, haloalkyl, and haloaryl, wherein the rosamine aldehyde is soluble in water.

10. The method according to claim 1, wherein the rosamine aldehyde comprises a composition having formula II:

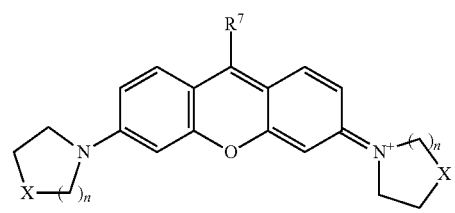

formula II wherein:
R⁷ is an aromatic or aromatically conjugated aldehyde,
wherein X is O, S, CH₂, CHR⁸, CR⁸R⁹ or NR⁸,
n is 1 or 2, and
R⁸ and R⁹ are each the same or different, selected from the group consisting of hydrogen, substituted or unsubstituted alkyl, aryl, heteroalkyl, heteroaryl, haloalkyl, and haloaryl;
wherein the rosamine aldehyde is water soluble, and substantially non-toxic to living cells at a concentration of less than about 100 µM.

11. The method according to claim 10, wherein X is CH₂, n is 1, and R⁷ is formylphenyl.

12. The method according to claim 10, wherein R⁷ is 4-formylphenyl, the rosamine aldehyde comprising (1-(9-(4-formylphenyl)-6-(pyrrolidin-1-yl)-3H-xanthen-3-ylidene)pyrrolidine, or its HCl salt: (1-(9-(4-formylphenyl)-6-(pyrrolidin-1-yl)-3H-xanthen-3-ylidene)pyrrolidinium chloride).

13. A method for labelling microtubules, comprising:
incubating alpha tubulin, a tubulin tyrosine ligase substrate having a hydrazine or hydrazide substituent, and tubulin tyrosine ligase for a sufficient time for a portion of the tubulin tyrosine ligase substrate having the hydrazine or hydrazide substituent to be ligated to alpha tubulin by the tubulin tyrosine ligase, whereby the alpha tubulin displays hydrazine or hydrazide substituents; and
after said incubating, adding a compound comprising rosamine aldehyde which spontaneously reacts with the hydrazine or hydrazine substituent, to form a hydrazone covalent bond.

14. The method according to claim 13, wherein the compound comprises a membrane permeable label, wherein the alpha tubulin and tubulin tyrosine ligase are produced within a living cell, and the membrane permeable label is provided in a medium outside the cell and enters the cell prior to ligation to the alpha tubulin.

15. The method according to claim 14, wherein the compound comprising rosamine aldehyde comprises a fluorescent dye, wherein the fluorescent dye is selectively ligated to alpha tubulin of microtubules of the living cell to form fluorescently labelled microtubules, further comprising capturing an image of the fluorescently labelled microtubules using a sub-diffraction microscopy technique.

16. The method according to claim 14, wherein the tubulin tyrosine ligase substrate comprises tyrosine hydrazide, and the rosamine aldehyde spontaneously reacts with the hydrazine functionality of the tyrosine hydrazide ligated to alpha tubulin, to form a hydrazone covalent bond linking the compound to the alpha tubulin within the living cell, substantially without toxicity to the living cell.

17. The method of claim 13, wherein the compound comprising rosamine aldehyde is a fluorescent dye, and the tubulin tyrosine ligase substrate having hydrazine or hydrazide substituent comprises tyrosine hydrazide.

18. A method for labelling alpha tubulin, comprising:
incubating the alpha tubulin with a tubulin tyrosine ligase substrate having a hydrazine or hydrazide substituent, in a medium containing tubulin tyrosine ligase, for a sufficient time, for a portion of the tubulin tyrosine ligase substrate having the hydrazine or hydrazide substituent to be ligated to alpha tubulin by the tubulin tyrosine ligase, whereby the alpha tubulin displays hydrazine or hydrazide substituents; and
after said incubating, adding a compound comprising rosamine aldehyde which spontaneously reacts with the hydrazine substituent, to form a hydrazone covalent bond linking the compound to the alpha tubulin.

19. The method according to claim 18, wherein:
the alpha tubulin and tubulin tyrosine ligase are present within a living cell, and the incubating and spontaneously reacting occurs substantially without toxicity to the cell;
the compound comprising rosamine aldehyde spontaneously reacts with the hydrazine substituent comprises a membrane permeable label which is supplied external to the cell;
further comprising capturing an image of the microtubules within the living cell comprising the alpha tubulin ligated to the tubulin tyrosine ligase substrate and covalently bonded to the membrane permeable label using a microscopy technique.

20. The method according to claim 19, wherein the compound comprising rosamine aldehyde comprises formula II:

formula II

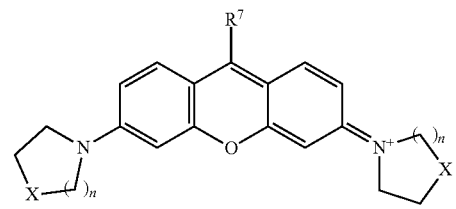

wherein:
R⁷ is an aromatic or aromatically conjugated aldehyde,
wherein X is O, S, CH₂, CHR⁸, CR⁸R⁹ or NR⁸,
n is 1 or 2, and
R⁸ and R⁹ are each the same or different, selected from the group consisting of hydrogen, substituted or unsubstituted alkyl, aryl, heteroalkyl, heteroaryl, haloalkyl, and haloaryl;
which is water soluble, and substantially non-toxic to living cells at a concentration of less than about 100 µM.

* * * * *